(12) United States Patent
Cheng et al.

(10) Patent No.: US 11,869,202 B2
(45) Date of Patent: *Jan. 9, 2024

(54) METHOD AND SYSTEM FOR PROCESSING MULTI-MODALITY IMAGE

(71) Applicant: SHANGHAI UNITED IMAGING HEALTHCARE CO., LTD., Shanghai (CN)

(72) Inventors: Zhaoning Cheng, Shanghai (CN); Rui Wang, Shanghai (CN); Weiwen Nie, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 119 days.

This patent is subject to a terminal disclaimer.

(21) Appl. No.: 17/347,531

(22) Filed: Jun. 14, 2021

(65) Prior Publication Data

US 2021/0312645 A1  Oct. 7, 2021

Related U.S. Application Data

(63) Continuation of application No. 16/236,596, filed on Dec. 30, 2018, now Pat. No. 11,037,309, which is a
(Continued)

(51) Int. Cl.
*G06T 7/30* (2017.01)
*G06T 7/174* (2017.01)
(Continued)

(52) U.S. Cl.
CPC ............ *G06T 7/30* (2017.01); *G06N 20/00* (2019.01); *G06T 5/50* (2013.01); *G06T 7/0012* (2013.01);
(Continued)

(58) Field of Classification Search
CPC ..... G06T 7/30; G06T 5/50; G06T 7/11; G06T 11/003; G06T 7/0012; G06T 7/174;
(Continued)

(56) References Cited

U.S. PATENT DOCUMENTS 11,037,309 B2 * 6/2021 Cheng ............... G06N 20/00
2008/0292164 A1 11/2008 Azar et al.
(Continued)

FOREIGN PATENT DOCUMENTS

CN 103617605 A 3/2014
CN 103815928 A 5/2014
(Continued)

OTHER PUBLICATIONS

International Search Report in PCT/CN2016/112689 dated Mar. 17, 2017, 8 pages.
(Continued)

*Primary Examiner* — Bernard Krasnic
(74) *Attorney, Agent, or Firm* — METIS IP LLC

(57) ABSTRACT

The present disclosure provides a method and system for processing multi-modality images. The method may include obtaining multi-modality images; registering the multi-modality images; fusing the multi-modality images; generating a reconstructed image based on a fusion result of the multi-modality images; and determining a removal range with respect to a focus based on the reconstructed image. The multi-modality images may include at least three modalities. The multi-modality images may include a focus.

20 Claims, 11 Drawing Sheets

Related U.S. Application Data continuation of application No. PCT/CN2016/112689, filed on Dec. 28, 2016.

(51) Int. Cl.
| | | |
|---|---|---|
| *G06T 7/00* | (2017.01) | |
| *G06T 11/00* | (2006.01) | |
| *G16H 30/40* | (2018.01) | |
| *G06N 20/00* | (2019.01) | |
| *G06T 7/11* | (2017.01) | |
| *G06T 5/50* | (2006.01) | |

(52) U.S. Cl.
CPC ............... *G06T 7/11* (2017.01); *G06T 7/174* (2017.01); *G06T 11/003* (2013.01); *G16H 30/40* (2018.01); *G06T 2207/10081* (2013.01); *G06T 2207/10088* (2013.01); *G06T 2207/10092* (2013.01); *G06T 2207/10104* (2013.01); *G06T 2207/20221* (2013.01); *G06T 2207/30016* (2013.01); *G06T 2207/30081* (2013.01); *G06T 2207/30096* (2013.01); *G06T 2207/30104* (2013.01)

(58) Field of Classification Search
CPC . G06T 2207/30081; G06T 2207/20221; G06T 2207/30096; G06T 2207/10092; G06T 2207/10104; G06T 2207/10081; G06T 2207/10088; G06T 2207/30016; G06T 2207/30104; G06N 20/00; G06N 20/20; G06N 5/003; G06N 5/025; G06N 20/10; G06N 5/048; G06N 7/005; G06N 5/046; G16H 30/40; G16H 20/40
USPC ........................................................ 382/131
See application file for complete search history.

(56) References Cited

U.S. PATENT DOCUMENTS

| | | | | |
|---|---|---|---|---|
| 2009/0253978 | A1* | 10/2009 | Hashimshony | G16H 30/20 600/407 |
| 2010/0260404 | A1 | 10/2010 | Ohishi | |
| 2013/0218024 | A1* | 8/2013 | Boctor | A61B 8/4416 600/476 |
| 2013/0266197 | A1* | 10/2013 | Nagenthiraja | G06T 7/149 382/128 |
| 2014/0161338 | A1* | 6/2014 | Machado | G06T 7/344 382/131 |
| 2014/0301621 | A1* | 10/2014 | Lu | G06K 9/46 382/131 |
| 2016/0196644 | A1 | 7/2016 | Peng et al. | |

FOREIGN PATENT DOCUMENTS

| | | |
|---|---|---|
| CN | 105488804 A | 4/2016 |
| CN | 105701799 A | 6/2016 |
| CN | 105849777 A | 8/2016 |
| CN | 105913375 A | 8/2016 |
| WO | 2009058915 A1 | 5/2009 |
| WO | 2014031531 A1 | 2/2014 |
| WO | 2015109331 A1 | 7/2015 |

OTHER PUBLICATIONS

Written Opinion in PCT/CN2016/112689 dated Mar. 17, 2017, 8 pages.

The Extended European Search Report in European Application No. 16925011.5 dated Oct. 31, 2019, 8 pages.

Brian C. Porter et al., Three-Dimensional Registration and Fusion of Ultrasound and MRI Using Major Vessels as Fiducial Markers, IEEE Transactions on Medical Imaging, 20(4): 354-359, 2001.

* cited by examiner

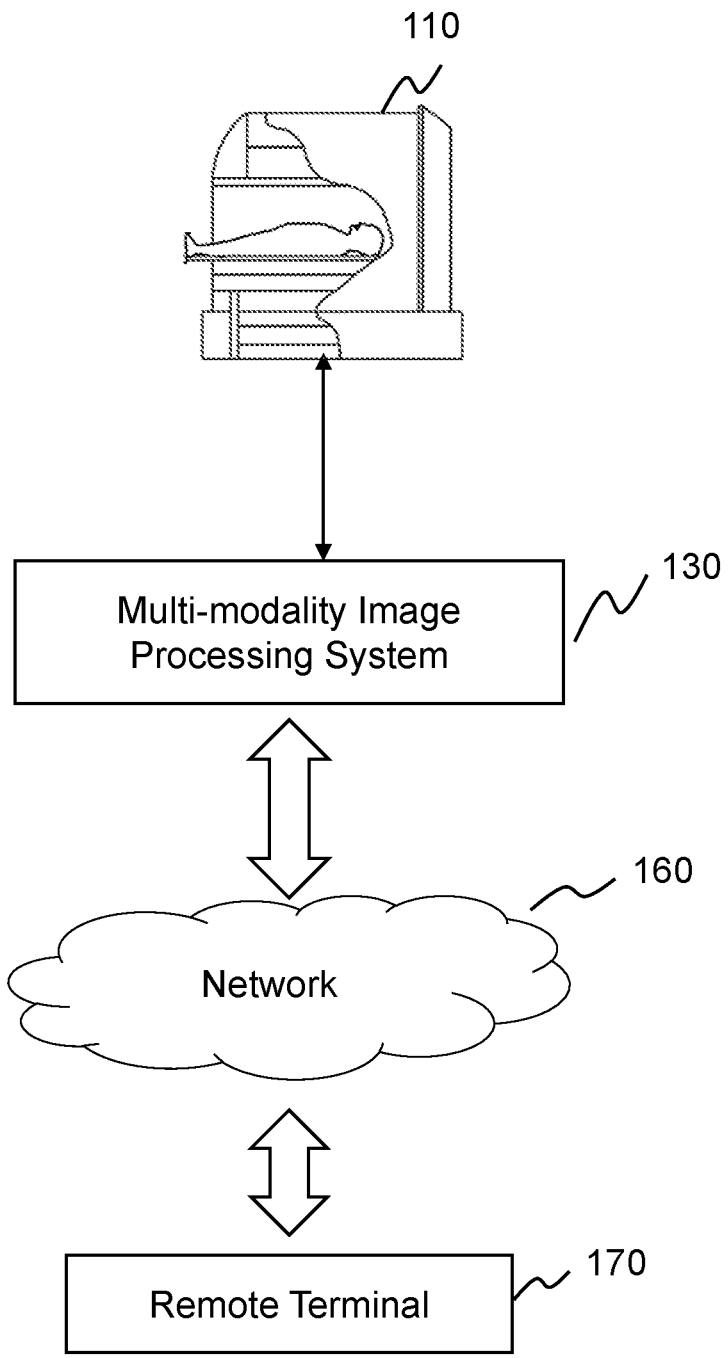
FIG. 1-A

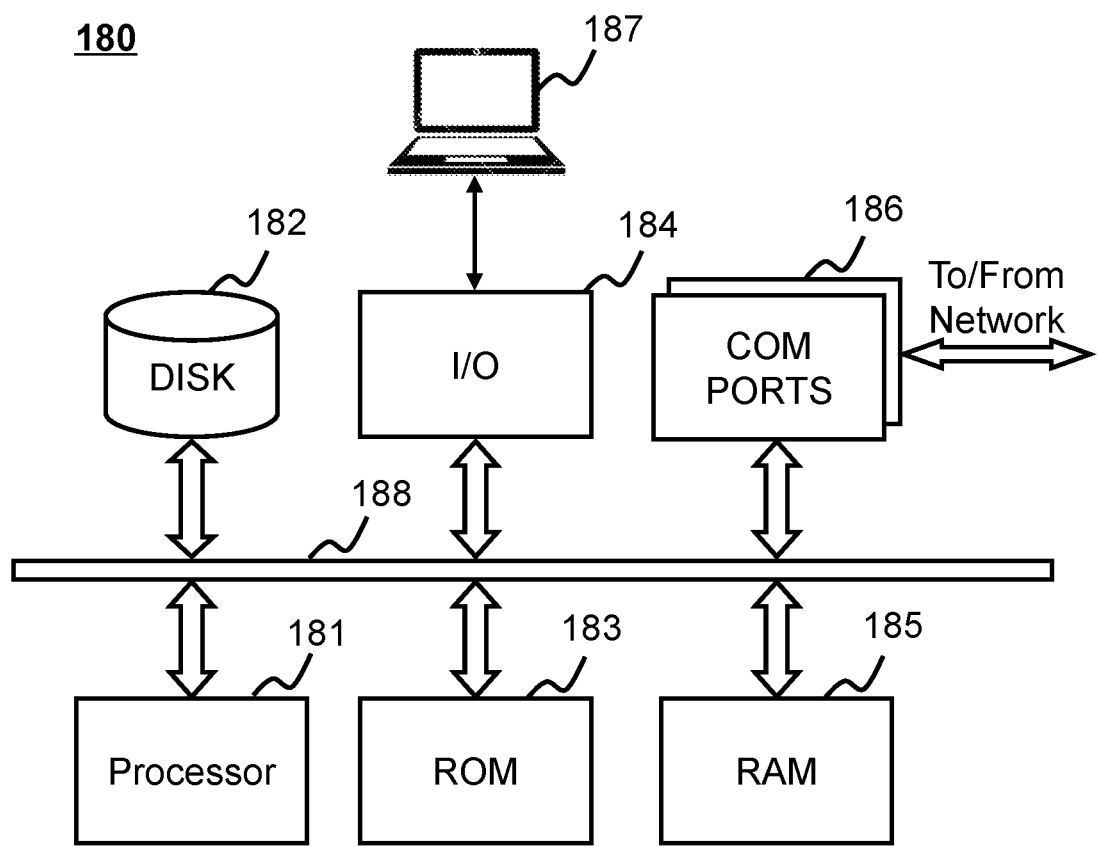
FIG. 1-B

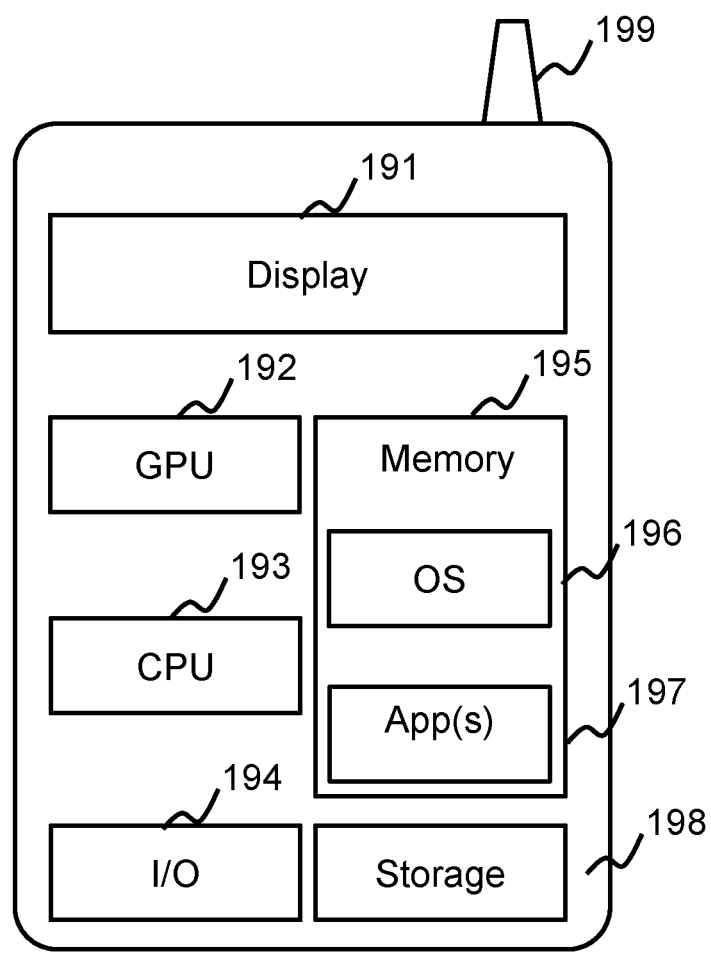
FIG. 1-C

US 11,869,202 B2

METHOD AND SYSTEM FOR PROCESSING MULTI-MODALITY IMAGE

CROSS-REFERENCE TO RELATED APPLICATIONS

This application is a continuation of U.S. application Ser. No. 16/236,596 filed on Dec. 30, 2018, which is a continuation of International Application No. PCT/CN2016/112689 filed on Dec. 28, 2016, the entire contents of each of which are hereby incorporated by reference.

TECHNICAL FIELD

The present disclosure generally relates to systems and methods for processing multi-modality images, and more particularly, to systems and methods for visualizing and analyzing multi-modality images of brain lesion tissue.

BACKGROUND

A doctor usually uses a medical imaging system to scan a patient's brain before performing a brain surgery, and imports scan results into a post-processing workstation to observe the scan results, thus assisting in diagnosis and guiding the surgery. Currently, a variety of brain-related scans can be provided, including Digital Subtraction Angiography (DSA), Magnetic Resonance Imaging (MRI), Blood Oxygenation Level Dependent Functional Magnetic Resonance Imaging (fMRI-BOLD), Diffusion Tensor Imaging (DTI), Diffusion Tensor Tractography (DTT), Magnetic Resonance Angiography (MRA), Computed tomography (CT), Positron Emission Tomography (PET), Single-Photon Emission Computerized Tomography (SPECT), Time of Flight Magnetic Resonance Imaging (TOF-MRI), Time of Flight Magnetic Resonance Angiography (TOF-MRA), Magnetoencephalography (MEG), Transcranial Magnetic Stimulation-Magnetic Resonance Imaging (TMS-MRI), fMRI-DTI, fMRI-DTT, PET-CT, SPET-CT, MRI-T1, MRI-T2, fMRI-DTI, fMRI-DTT, or the like, or any combination thereof.

The multi-modality analysis function of nerve fibers and the fusion function of multi-modality images provided by a current medical post-processing workstation are mainly for the processing and analysis of two-modality image data. The multi-modality analysis of nerve fibers mainly combines the MRI-T1, fMRI-BOLD or fMRI-DTI/DTT multi-modality information, so as to analyze the structure of the cranial nerve in the brain and the association with the functional region. The fusion of multi-modality images mainly combines a CT image and a PET-CT image to analyze a patient's tumor metabolic intensity and diffusion. In order to provide a wide range of focus information for a doctor, assist the doctor in diagnosing the disease, and guide the surgery, it is necessary to perform a comprehensive data analysis of multi-modality (e.g., three or more modalities) image data.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

An aspect of the present disclosure relates to a method for processing multi-modality images. The method for processing multi-modality images may be implemented on at least one machine. Each of the at least one machine may include at least one processor and a storage. The method for processing multi-modality images may include one or more of the following operations: obtaining multi-modality images including at least three modalities, the multi-modality images including a focus; registering the multi-modality images; fusing the multi-modality images; generating a reconstructed image based on a fusion result of the multi-modality images; and determining a removal range with respect to the focus based on the reconstructed image.

Another aspect of the present disclosure relates to a non-transitory computer readable medium. The non-transitory computer readable medium may include at least one set of instructions. When executed by one or more processors, the at least one set of instructions directs the one or more processors to perform acts of a method for processing multi-modality images.

Yet another aspect of the present disclosure relates to a system for processing multi-modality images. The system for processing multi-modality images may include at least one processor and at least one set of instructions. When executed by the at least one processor, the at least one set of instructions directs the at least one processor to perform acts of a method for processing multi-modality images.

In some embodiments, the system for processing multi-modality images may further include the non-transitory computer readable medium.

In some embodiments, the method for processing multi-modality images may further include: displaying image information based on the multi-modality images or the reconstructed image.

In some embodiments, the method for processing multi-modality images may further include: obtaining a standard image, the standard image including standard image data associated with a part of a target object; and/or registering the multi-modality images based on the standard image.

In some embodiments, the multi-modality images may include multi-modality brain images, and the standard image may include a standard brain image.

In some embodiments, the displaying image information may include: displaying information relating to blood vessels of a brain, nerve fibers, a functional region of the brain, or a metabolic rate of brain tissue.

In some embodiments, the multi-modality images may further include a magnetic resonance imaging (MRI) T1 image, a blood oxygenation level dependent (BOLD) image, and a first image, and the first image includes one of a diffusion tensor imaging (DTI)/diffusion tensor tractography (DTT) image, a computed tomography (CT)/positron emission tomography (PET) image, or an MRI Time of Flight (TOF) image.

In some embodiments, the registering the multi-modality images may include: generating a second image by registering the BOLD image based on the standard image; generating a third image by registering the first image based on the MRI T1 image; and registering the second image and the third image based on the MRI T1 image.

In some embodiments, the generating a reconstructed image may include: segmenting the fusion result of the multi-modality images; and generating the reconstructed image by a reconstruction algorithm based on the segmented multi-modality images, the reconstruction algorithm including multi-planar reconstruction (MPR) or volume rendering (VR).

In some embodiments, the determining a removal range of the focus may include: determining a range of the focus based on the reconstructed image; determining first surrounding information of the focus based on the range of the focus, the first surrounding information including information relating to a surrounding blood vessel, information relating to a surrounding nerve, or any information relating to a tissue or organ in a vicinity of the focus; and determining the removal range based on the first surrounding information.

In some embodiments, the method for processing multi-modality images may further include simulating removal of the focus based on the removal range.

In some embodiments, the determining the removal range may further include: determining second surrounding information after the focus is removed; determining, based on the first surrounding information and the second surrounding information, injury information of a surrounding tissue or organ of the focus after the focus is removed; and optimizing the removal range based on the injury information.

In some embodiments, the method for processing multi-modality images may further include: determining a surgery plan based on the removal range.

In some embodiments, the focus may include a brain tumor, and the first surrounding information or the second surrounding information may further include a name of a blood vessel that the focus passes through, a blood flow rate of the blood vessel, a count of brain fibers that are affected by the focus, a connection of the brain fibers, or a name of a brain functional region that is covered by the focus.

In some embodiments, the injury information may include injury information of the blood vessel after the focus is removed, injury information of the brain fibers after the focus is removed, or injury information of the brain functional region after the focus is removed.

In some embodiments, the method for processing multi-modality images may further include storing case information associated with the focus, the case information including the multi-modality images, the reconstructed image, the range of the focus, the optimized removal range, the first surrounding information, the second surrounding information, the injury information, information associated with the focus, information associated with the surgery plan, or information associated with post-surgery recovery.

In some embodiments, the method for processing multi-modality images may further include retrieving a similar case based on the case information.

In some embodiments, the storing the case information associated with the focus may include storing the case information in a database; and wherein the retrieving the similar case comprises retrieving the similar case from the database.

In some embodiments, the method for processing multi-modality images may further include optimizing the removal range by machine leaning based on information in the database.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a schematic diagram illustrating an exemplary image analysis system according to some embodiments of the present disclosure;

FIG. 1-B is a schematic diagram illustrating exemplary hardware components of a computing device according to some embodiments of the present disclosure;

FIG. 1-C is a schematic diagram illustrating exemplary hardware components of a mobile device according to some embodiments of the present disclosure;

DETAILED DESCRIPTION

Figure 2:
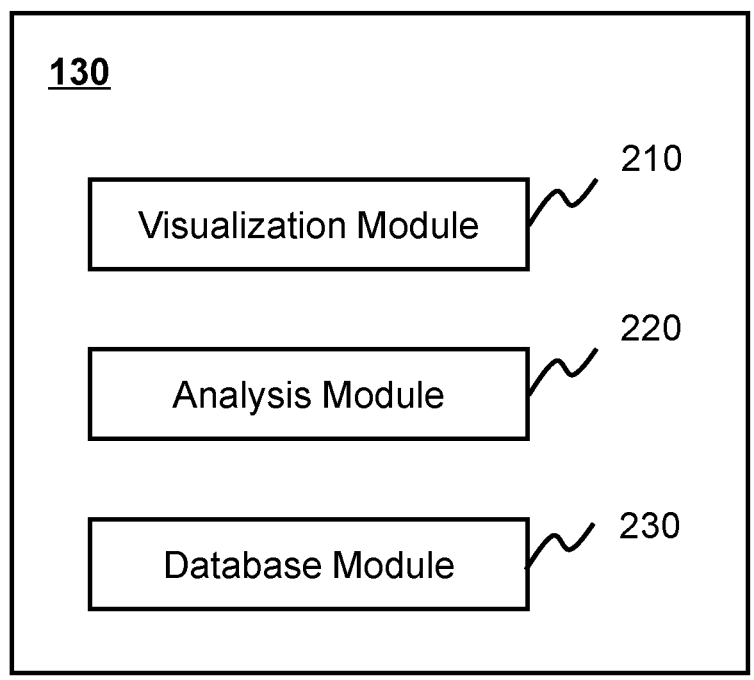
FIG. 2 is a schematic diagram illustrating an exemplary multi-modality image processing system according to some embodiments of the present disclosure.

In the present disclosure and claims, the words "a/an", "one", "a kind of" and/or "the" are not specifically singular, and may include plural numbers unless otherwise indicated obviously from the context. In general, terms "comprise" and "include" only indicate those steps and elements that have been explicitly identified, and such steps and elements do not constitute an exclusive list, the method or the device may also include other steps or elements.

Although the present disclosure makes various references to certain modules in a multi-modality image processing system according to an embodiment of the present disclosure, any number of different modules may be used and run on a remote terminal and/or a server connected to the system via a network. The modules are merely illustrative, and different aspects of the system and method may use different modules.

Flowcharts are used in the present disclosure to illustrate operation steps performed by a multi-modality image processing system according to an embodiment of the present disclosure. It should be understood that the operation steps shown at the front or at the rear are not necessarily performed in order. On the contrary, various steps may be executed in reverse order or at the same time. At the same time, other operation steps may be added to these processes, or a step or a few steps may be removed from these processes.

In a multi-modality image processing system, "multi-modality images" may include two or more modalities. The modalities may include Digital Subtraction Angiography (DSA), Magnetic Resonance Imaging (MRI), Blood Oxygenation Level Dependent Functional Magnetic Resonance Imaging (fMRI-BOLD), Diffusion Tensor Imaging (DTI), Diffusion Tensor Tractography (DTT), Magnetic Resonance Angiography (MRA), Computed tomography (CT), Positron Emission Tomography (PET), Single-Photon Emission Computerized Tomography (SPECT), Time of Flight Magnetic Resonance Imaging (TOF-MRI), Time of Flight Magnetic Resonance Angiography (TOF-MRA), Magnetoencephalography (MEG), Ultrasonography (US), Transcranial Magnetic Stimulation-Magnetic Resonance Imaging (TMS-MRI), MRI-T1, MRI-T2, fMRI-DTI, fMRI-DTT, CT-PET, CT-SPET, DSA-MR, PET-MR, PET-US, SPECT-US, US-CT, US-MR, X-ray-CT, X-ray-PET, X-ray-US, or the like, or any combination thereof. In some embodiments, a target object displayed on the multi-modality images may be an organ, a body, an object, a lesion, a tumor, or the like, or any combination thereof. In some embodiments, the target object displayed on the multi-modality images may be lesion tissue of the brain. In some embodiments, the multi-modality images may be two-dimensional images and/or three-dimensional images. In a two-dimensional image, the smallest resolvable element may be a pixel. In a three-dimensional image, the smallest resolvable element may be a voxel. In a three-dimensional image, an image may include a series of two-dimensional slices or two-dimensional layers.

FIG. 1-A is a schematic diagram illustrating an exemplary image analysis system according to some embodiments of the present disclosure. The image analysis system 100 may include an imaging device 110, a multi-modality image processing system 130, a network 160, and a remote terminal 170. In some embodiments, the imaging device 110, the multi-modality image processing system 130, and the remote terminal 170 may be directly connected and/or indirectly connected to each other. In some embodiments, the imaging device 110, the multi-modality image processing system 130, and the remote terminal 170 may be directly connected and/or indirectly connected to each other via the network 160. In some embodiments, the imaging device 110, the multi-modality image processing system 130, and the remote terminal 170 may be indirectly connected via one or more intermediate units (not shown). The intermediate unit may be an entity (e.g., a device, an apparatus, a module, an interface, or the like, or any combination thereof), or may be a non-entity (e.g., radio waves, optical, sonic, electromagnetic, or the like, or any combination thereof), or the like, or any combination thereof. Difference modules and units may be connected by wireless and/or wired means.

The imaging device 110 may scan a target object, and generate data and an image associated with the target object. The imaging device 110 may further process the image using the generated data. In some embodiments, the target object may include a human body, an animal, or a portion thereof, such as an organ, tissue, a lesion site (e.g., a tumor site), or any combination thereof. For example, the target object may be a head, a chest, an abdomen, a heart, a liver, an upper limb, a lower limb, a vertebra, a bone, a blood vessel, or the like, or any combination thereof. In some embodiments, the imaging device 110 may be a device or a device group. In some embodiments, the imaging device 110 may be a medical imaging device, such as an MRI device, a SPECT device, a CT device, a PET device, or the like. In some embodiments, the medical imaging device may be used alone and/or in combination, such as a SPECT-MRI device, a CT-PET device, a SPET-CT device, or the like. The imaging device 110 may include a scanner that scans the target object and obtains information (e.g., images, data, etc.) associated with the target object. In some embodiments, the imaging device 110 may be a radioactive scanning device. The device may include a radioactive scanning source that emits radioactive rays to the target object. The radioactive rays may include corpuscular rays, photon rays, or the like, or any combination thereof. The corpuscular rays may include neutrons, protons, alpha rays, electrons, p media, heavy ions, or the like, or any combination thereof. The photon rays may include X-rays, y-rays, ultraviolet rays, lasers, or the like, or any combination thereof. In some embodiments, the photon rays may be X-rays; the corresponding imaging device 110 may be a CT system, a digital radiography system (DR), a multi-modality medical imaging system, or the like, or any combination thereof. In some embodiments, the multi-modality medical imaging system may include a CT-PET system, a SPECT-MRI system, a SPET-CT system, or the like, or any combination thereof. In some embodiments, the imaging device 110 may include a ray generation unit and a ray detection unit (not shown). For example, the imaging device 110 may include a photon detector to perform the generation and/or detection of rays. The photon detector may generate photons for scanning the target object or capture the photons after the target object is scanned. In some embodiments, the imaging device 110 may be a PET system or a multi-modality medical imaging system, and the photon detector thereof may include a scintillator and/or a photodetector. In some embodiments, the imaging device 110 may include a radio frequency transmitting coil and/or a radio frequency receiving coil (not shown). For example, the imaging device 110 may be an MRI imaging device.

The multi-modality processing system 130 may process information from the imaging device 110, the network 160, and/or the remote terminal 170. The information may include image information generated by the imaging device 110 or information related to a patient, information transmitted by a cloud device (not shown) via the network 160, commands and information issued by the remote terminal 170, or the like, or any combination thereof. In some embodiments, the multi-modality image processing system 130 may perform various operations related to multi-modality image data processing, such as registration and fusion of multi-modality image data, division of the multi-modality image data, reconstruction of images, analysis based on the reconstructed image data, storage of the multi-modality image data, retrieval of the multi-modality image data, or the like, or any combination thereof. In some embodiments, the multi-modality image processing system 130 may reconstruct one or more two-dimensional and/or three-dimensional images based on the information. In some embodiments, the reconstructed image may include focus information, and the multi-modality image processing system 130 may analyze the reconstructed image based on the focus information to simulate a procedure of a surgery. For example, the multi-modality image processing system 130 may select a removal range with respect to the focus by analyzing the image. As another example, the multi-modality image processing system 130 may analyze the damage to surrounding tissue after the removal of the focus in the image, thereby further optimizing the focus removal range in the image, and avoiding or reducing the damage to the surrounding tissue after the removal of the focus. In addition, the multi-modality image processing system 130 may store or query multi-modality images. For simplicity, in the following description, a portion corresponding to an organ or tissue in an image is referred to as an organ or tissue; a treatment of the corresponding portion in the image is referred to as a treatment of the organ or the tissue. In some embodiments, the multi-modality image processing system 130 may implement its function by one or more computing devices 180 having hardware components. FIG. 1-B is a schematic diagram illustrating exemplary hardware components of a computing device according to some embodiments of the present disclosure.

The network 160 may be a single network, or any combination of multiple different networks. For example, the network 160 may be a Local Area Network (LAN), a Wide Area Network (WAN), a Public Switched Telephone Network (PSTN), a Virtual Network (VN), a Private Network (PN), a Metropolitan Area Network (MAN), or any combination thereof. The network 160 may include a plurality of network access points and may use wired network architecture, wireless network architecture and wired/wireless network hybrid architecture. The wired network may include a metal cable, a hybrid cable, an optical cable, or the like, or any combination thereof. The wireless network may include Bluetooth™, Wi-Fi, ZigBee, Near Field Communication (NFC), cellular networks (e.g., Global System for Mobile communication (GSM), Code Division Multiple Access (CDMA), 3G, or 4G, etc.), or the like, or any combination thereof. The network 160 may be within the scope of the present disclosure, but is not limited to the description.

The remote terminal 170 may receive, operate, process, store or display the multi-modality image data. The remote terminal 170 may communicate with the imaging device 110 and the multi-modality image processing system 130 via the network 160. In some embodiments, the remote terminal 170 may be used by one or more users, for example, a hospital medical care worker, a medical school and its students, other trained non-medical care workers, or the like, or any combination thereof. In some embodiments, the remote terminal 170 may be a device terminal connected to the imaging device 110, the multi-modality image processing system 130, and the network 160, such as a display screen, a printer, a computing device, or the like, or any combination thereof. In some embodiments, the remote terminal 170 may be a computing device 180 or a mobile device 190 having hardware components. FIG. 1-C is a schematic diagram illustrating exemplary hardware components of a mobile device according to some embodiments of the present disclosure.

It should be noted that the above description of the image analysis system 100 is for convenience of description only, and cannot limit the present disclosure within the scope of the illustrated embodiments. It should be understood by those skilled in the art that after understanding the principle of the system, each module may be arbitrarily combined, a subsystem may be connected with other modules, and various modifications and changes may be made in the form and detail of the application field of the above method and system without departing from the principle. For example, the multi-modality image processing system 130 and the remote terminal 170 may be integrated on a computing device and/or a mobile device. As another example, the image analysis system 100 may include two or more imaging devices 110. As another example, the image analysis system 100 may include two or more remote terminals 170.

FIG. 1-B is a schematic diagram illustrating exemplary hardware components of a computing device according to some embodiments of the present disclosure. The computing device 180 may realize and/or implement a particular system (e.g., the multi-modality image processing system 130) disclosed in the present disclosure. The particular system in the present embodiment explains a hardware platform that includes a user interface using a functional block diagram. The computing device 180 may implement one or more components, modules, units, subunits (e.g., the remote terminal 170, the multi-modality image processing system 130, etc.) of the image analysis system 100. The computing device 180 may be a computer of a general purpose, or a computer of a particular purpose. Both computers may be used to implement the particular system in the present embodiment. For simplicity, only one computing device is shown in FIG. 1-B, but a related calculation function for providing the information required for the multi-modality image processing described in the present embodiment may be a processing load of a decentralized system that may be performed by a group of similar platforms in a distributed manner.

As shown in FIG. 1-B, the computing device 180 may include an internal communication bus 188, a processor 181, a hard disk 182, a read only memory (ROM) 183, an input/output (I/O) 184, a random access memory (RAM) 185, a communication port 186, and a user interface 187. The internal communication bus 188 may enable data communication between the components of the computing devices 180. The processor 181 may execute program instructions and/or complete any function, component, module, unit, subunit of the image analysis system 100 described in this disclosure. The processor 181 may include one or more processors. In some embodiments, the processor 181 may include a microcontroller, a simplified instruction system computer (RISC), an application specific integrated circuit (ASIC), a specific application instruction set processor (ASIP), a central processing unit (CPU), a graphics processor (GPU), a physical processor (PPU), a microprocessor unit, a digital signal processor (DSP), a field programmable gate array (FPGA), or other circuitry or processors capable of executing computer program instructions, or the like, or any combination thereof.

In some embodiments, the processor 181 may control the imaging device 110, the multi-modality image processing system 130, and/or the remote terminal 170. In some embodiments, the processor 181 may control the imaging device 110, the multi-modality image processing system 130, and the remote terminal 170 to receive information from or send information to the above system/device. In some embodiments, the processor 181 may receive image information that is from the imaging device 110, or information related to the target object. In some embodiments, the processor 181 may send the image information or the information related to the target object to the multi-modality image processing system 130. The processor 181 may receive processed data or images from the multi-modality image processing system 130. The processor 181 may send processed data or images to the remote terminal 170. In some embodiments, the processor 181 may execute programs, algorithms, software, or the like. In some embodiments, the processor 181 may include one or more interfaces. The interface may include an interface connecting the imaging device 110, the multi-modality image processing system 130, the remote terminal 170, and/or other components, modules or units in the image analysis system 100.

In some embodiments, the processor 181 may execute a command from the remote terminal 170. The processor 181 may control the imaging device 110 and/or the multi-modality image processing system 130 by processing and/or converting the above command. For example, the processor 181 may process information input by the user through the remote terminal 170 and convert the information into one or more corresponding commands. The command may be a scan time, scan target location information, a rotation speed of a support of the imaging device 110, a scan parameter, or the like, or any combination thereof. The processor 181 may control the multi-modality image processing system 130 to select different algorithms to process and/or analyze the image data. In some embodiments, the processor 181 may be integrated in an external computing device to control the imaging device 110, the multi-modality image processing system 130, and/or the remote terminal 170, or the like.

In some embodiments, the computing device 180 also includes one or more kinds of storage devices for storing data, programs, and/or algorithms, or the like, such as the hard disk 182, the ROM 183, the random access storage (RAM) 185, a cloud storage, or the like. The storage device may be used by various data files in computer processing and/or communication, and possible program instructions executed by the processor 181. The storage device may be internal to the image analysis system 100 or external to the image analysis system 100 (e.g., the external storage device connected via the network 160, or a cloud storage, etc.). The storage device (e.g. the hard disk 182, the ROM 183, the RAM 185, a cloud storage, etc.) may store information from the imaging device 110, the multi-modality image processing system 130, and the remote terminal 170. The information may include a plurality of modality images, patient-related information, standard images and related information, programs, software, algorithms, data, texts, numbers, images, audio used in the multi-modality image processing, or any combination thereof.

The hard disk 182 may be a device that stores information using magnetic energy. In some embodiments, the hard disk 182 may also be other devices that store information using magnetic energy, such as a floppy disk, a magnetic tape, a magnetic core memory, a bubble memory, a U disk, a flash memory, or the like. The ROM 183 and/or the RAM 185 may be a device that uses electrical energy to store information. The ROM 183 may include an optical disk drive, a hard disk, a tape, an early Non-Volatile Random Access Memory (NVRAM), a nonvolatile Static Random Access Memory (SRAM), a flash memory, an erasable rewritable read only memory, an erasable programmable read only memory, a programmable read-only memory, or the like, or any combination thereof. The RAM 185 may include a Dynamic Random Access Memory (DRAM), an SRAM, a Thyristor Random Access Memory (T-RAM), a Zero capacitor Random Access Memory (Z-RAM), or the like, or any combination thereof.

In some embodiments, the storage device may also be a device that optically stores information, such as a CD or a DVD, or the like. In some embodiments, the storage device may be a device that stores information using magneto-optical means, such as a magneto-optical disk, or the like. The access mode of the above storage device may be random storage, serial access storage, read only storage, or the like, or any combination thereof. The above storage device may be a non-permanent memory storage device or a permanent memory storage device. The above-mentioned storage devices are just a few examples, and the storage devices are not limited thereto. The above storage devices may be local or remote. The above storage devices may be centralized or distributed. For example, the above storage devices may be provided on a cloud server.

The I/O 184 may support I/O data streams between the computing device 180 and other components of the image analysis system 100 (e.g., the imaging device 110, the remote terminal 170, etc.), such as receiving, sending, displaying, or printing information. In some embodiments, the I/O 184 may include a keyboard, a touch device, a mouse, a mechanical analog device, a wearable device (e.g., 3D glasses, mechanical gloves, etc.), a virtual reality device, an audio input device, an image input device, a remote control device, or the like, or any combination thereof. The output information may be sent to the user, or not sent to the user. The output information not to be sent may be stored in the hard disk 182, the ROM 183, and the RAM 185, or may be deleted. In some embodiments, the user may input some original parameters through the I/O 184 or set initialization conditions for the corresponding multi-modality image processing. In some embodiments, some input information may be from an external data source (e.g., a floppy disk, a hard disk, an optical disk, a memory chip, a wired terminal, a wireless terminal, or the like, or any combination thereof). The I/O 184 may receive information from other modules or units in the image analysis system 100 or send information to other modules or units in the system.

The communication port 186 may enable data communication between the computing device 180 and other components of the image analysis system 100 (e.g., the imaging device 110, the remote terminal 170, etc.). The computer may send and receive information and data from the network 160 via the communication port 186. The form of the output information of the image analysis system 100 may include numbers, characters, instructions, pressure, sound, images, systems, software, programs, or the like, or any combination thereof.

The user interface 187 may display staged information of the multi-modality image processing process, or the multi-modality image processing result (e.g., a cross-sectional view, a multi-plane image reconstructed by the multi-modality images, or the like, or any combination thereof). The user interface 187 may provide a prompt for a user input parameter or help the user participate in the multi-modality image processing process (e.g., initiate or stop processing, select or modify operational parameters, select or modify algorithms, modify programs, exit a system, maintain a system, upgrade a system, or update a system, etc.).

It should be noted that the above storage device (e.g., the hard disk 182, the ROM 183, the RAM 185, the cloud storage, etc.), and/or the processor 181 may actually exist in the system, or complete a corresponding function through a cloud computing platform. The cloud computing platform may include a data storage based storage cloud platform, a data processing based computing cloud platform and a comprehensive cloud computing platform that combines data storage and processing. The cloud platform used by the image analysis system 100 may be a public cloud, a private cloud, a community cloud, a hybrid cloud, or the like. For example, according to actual needs, a portion of the information received by the image analysis system 100 may be calculated and/or stored by the cloud platform; and the other portion of the information may be calculated and/or stored by a local processing device and/or a storage device.

In some embodiments, the image analysis system 100 may have one or more computing devices 180. The computing devices 180 may realize and/or implement the same or different functions. For example, the first computing device may control the imaging device 110 to scan the target object and obtain the multi-modality image data; and the second computing device may acquire the multi-modality image data from the first computing device or other storage devices and process and/or analyze the multi-modality image data.

FIG. 1-C is a schematic diagram illustrating exemplary hardware components of a mobile device according to some embodiments of the present disclosure. The mobile device 180 may realize and/or implement a particular system disclosed in the present disclosure. In some embodiments, the remote terminal 170 for displaying and interacting with location-related information may be a mobile device 190. The mobile device 190 may have a variety of forms including smartphones, tablet PCs, music players, portable game consoles, Global Positioning System (GPS) receivers, wearable computing devices (e.g., eyeglasses, watches, etc.), or the like, or any combination thereof. In some embodiments, the mobile device 190 may include one or more antennas 199 (e.g., a wireless communication unit), a display 191, a Graphics Processing Unit (GPU) 192, a Central Processing Unit (CPU) 193, an I/O 194, a memory 195, and a storage 198. In some embodiments, the mobile device 190 may also include any other suitable component, such as a system bus or a controller (not shown). As shown in FIG. 1-C, a mobile operating system 196, such as iOS, Android, Windows Phone, or the like, and/or one or more applications 197 may be loaded from the storage 198 into the memory 195 and executed by the CPU 193. The application 197 may include a browser and/or other mobile applications suitable for receiving and processing image-related information on the mobile device 190. The I/O 194 may provide an interactive function of information related to the multi-modality images. The I/O 194 may realize information interaction between the mobile device 190 and the multi-modality image processing system 130, and/or other components of the image analysis system 100, for example, perform information transmission via the network 160.

In order to implement different modules, units, and their functions described in previous disclosures, the computing device 180 and/or the mobile device 190 may act as a hardware platform for one or more of the components described above (e.g., the multi-modality image processing system 130, the remote terminal 170, and/or other components of the image analysis system 100 described in FIG. 1-A). The hardware elements, operating systems, and programming languages of such computers are common in nature and it may be assumed that those skilled in the art are familiar with these techniques and can use the techniques described herein to provide the information required for the multi-modality image processing. A computer that includes user interface elements can be used as a personal computer (PC) or other types of workstations or terminal devices, and can be used as a server after being properly programmed. It should be noted that those skilled in the art are familiar with such structures, programs, and general operations of such computer devices, and therefore all drawings do not require additional explanation.

FIG. 2 is a schematic diagram illustrating an exemplary multi-modality image processing system according to some embodiments of the present disclosure. The multi-modality image processing system 130 may include a visualization module 210, an analysis module 220, and a database module 230. It may be apparent that the multi-modality image processing system 130 described in FIG. 2 may merely represent some embodiments of the present disclosure, for those of ordinary skill in the art, modifications, additions and deletions may be made according to the description of the multi-modality image processing system 130 without making creative efforts. For example, two modules can be combined as one module; alternatively, one module may be segmented into two or more modules.

The visualization module 210 may visualize multi-modality images. The visualization module 210 may be connected to the analysis module 220, the database module 230, and/or other related modules (not shown). The multi-modality images may refer to images of two or more different modalities. The images of different modalities may refer to images generated by different devices using different imaging principles, or by the same imaging device in different imaging modes. In some embodiments, the multi-modality images may include images including various modalities, for example, any combination of two or more of an MRI image, a CT image, an MRA image, an fMRI image, a PET image, a DTI/DTT image, a CT-PET image, an fMRI-DTI image, a TOF-MRI image, a TOF-MRA image, or the like. The multi-modality images may be acquired from the imaging device 110, the processor 181, the storage device (e.g., the hard disk 182, the ROM 183, the RAM 185, a cloud storage, etc.), the I/O 184, or the remote terminal 170, or acquired from an external data source via the network 160. In some embodiments, visual multi-modality images may be obtained from experiments (e.g., medical experiments, clinical simulation experiments, industrial test experiments, etc.), generated by the imaging device 110, or synthesized by computation and simulation. In some embodiments, the visualization module 210 may perform processing such as registration, fusion, and/or reconstruction to the multi-modality images. In some embodiments, the visualization module 210 may visualize the multi-modality images based on one or more visualization techniques. The visualization techniques of the multi-modality images may be, according to different description methods of data in the process, a surface rendering technique, a volume rendering technique, and a hybrid rendering technique. The surface rendering technique may reconstruct the surface of an object. For example, the surface rendering is realized using a graphics technique based on isosurface data of a three-dimensional data field obtained by multi-modality image data segmentation. The volume rendering technique may use a voxel as a basic unit, and generate a three-dimensional object image directly from three-dimensional data to represent internal information of an object. The hybrid rendering technique may fuse reconstruction algorithms of the surface rendering and the volume rendering to perform surface and internal synchronous reconstruction. In some embodiments, visualization results of the multi-modality images through the visualization module 210 may be stored in a storage device (e.g., the hard disk 182, the ROM 183, the RAM 185, the cloud storage, etc.) to provide information for subsequent analysis of the multi-modality images. In some embodiments, the visualization results of the multi-modality images through the visualization module 210 may be analyzed in real time through the analysis module 220.

The analysis module 220 may analyze the multi-modality images. The analysis module 220 may be connected to the visualization module 210, the database module 230, and/or other related modules (not shown). In some embodiments, the analysis module 220 may analyze one or more modality images in the multi-modality images separately, or perform comprehensive analysis of a reconstructed image of the multi-modality images. In some embodiments, the analysis module 220 may analyze a part of and/or overall information of the target object displayed in the multi-modality images, for example, tissue function information of the target object, spatial structure information of the target object, physiological information of the target object, or the like, or any combination thereof. The tissue function information may include whether the physiological function of tissue or an organ is abnormal, whether a lesion is present, the degree of the lesion, or the like, or any combination thereof. The spatial structure information may include two-dimensional and/or three-dimensional anatomical structure information, for example, morphology, a count, a size, a location, or the like, or any combination thereof. The physiological information may include the metabolic rate of the tissue or organ, a name of a blood vessel that a lesion site passes through, a blood flow rate of the blood vessel, a blood flow velocity, or the like, or any combination thereof. In some embodiments, the analysis module 220 may analyze surrounding information of a focus in the multi-modality images and determine injury information after the focus is removed to aid for subsequently determining a surgical simulation plan. The surrounding information of the focus may include information relating to blood vessels surrounding the focus, information relating to nerves surrounding the focus, or information relating to tissue or organs surrounding the focus, or the like, or any combination thereof. The injury information after the focus is removed may include injury information of the blood vessels after the focus is removed, injury information of the nerves after the focus is removed, or injury information of the organs or the tissue after the focus is removed, or the like, or any combination thereof. In some embodiments, the analysis module 220 may generate an analysis report according to a result of the analysis. The analysis report may be sent to a storage device (e.g., the hard disk 182, the ROM 183, the RAM 185, the cloud storage, etc.), the I/O 184, and/or the remote terminal 170.

The database module 230 may store and/or retrieve information. The database module 230 may include one or more databases. The database module 230 may be connected to the visualization module 210, the analysis module 220, or other related modules (not shown). In some embodiments, the information stored in the database module 230 may include basic information about a patient corresponding to the multi-modality images, case information of the target object displayed on the multi-modality images, information related to the multi-modality images, or the like, or any combination thereof. The basic information may include a patient's name, sex, age, medical history, biochemical examination information, or the like, or any combination thereof. The case information may include an image, an image analysis result, focus-related information, a surgery plan, postoperative recovery information, or the like, or any combination thereof. The information related to the multi-modality images may include a generation time of the multi-modality images, a generation time of an examination result of the multi-modality images, a system analysis time of the multi-modality images, a surgical operation time of a patient, or the like, or any combination thereof. In some embodiments, the database module 230 may store information from the imaging device 110, the processor 181, the storage device (e.g., the hard disk 182, the ROM 183, the RAM 185, a cloud storage, etc.), the I/O 184, the remote terminal 170, the visualization module 210, the analysis module 220, or the like.

In some embodiments, the database module 230 may store the above information in a data table. A database may include one or more data tables. The data table may include one or more rows, and/or one or more columns. The above information may be stored in a row or a column in the data table. The data table may perform classified storage on the above information. For example, the basic information of one or more patients, the case information of one or more target objects, or the information related to the multi-modality images may be stored in different data tables. The database module 230 may create a connection between two or more data tables to facilitate the database module 230 to find the corresponding information of a second data table through the information in a first data table. For example, if the first data table includes x patients' names and the second data table includes the x patients' surgery plans, the database module 230 may store the same patient's name and surgery plan in the same row or column of the first data table and the second data table, respectively, and the database module 230 may find the patient's surgery plan based on the patient's name. As another example, the database module 230 may set a same eigenvalue or number for the same patient's name and surgery plan, and the information of the same patient may be associated by the eigenvalue or number. In some embodiments, the database module 230 may create an index for the stored information. A database may include one or more indexes. The index may refer to a data structure that sorts one or more columns of information in the data table. The data structure may adopt a B-Tree structure or a B+Tree structure. The search of information may be facilitated through the index.

In some embodiments, the database module 230 may perform keyword retrieval and/or automatic retrieval based on one or more kinds of stored information. The retrieval of the keyword may be performed based on one or more keywords (e.g., the basic information of the patient corresponding to the multi-modality images, the case information of the target object displayed on the multi-modality images, the information related to the multi-modality images, etc.) provided by the user. The automatic retrieval may be an automatic classified retrieval performed by the database module 230 based on one or more criteria, for example, the same or similar image modality, the same or similar image analysis result, the same or similar surgery plan, the generation time of the same or similar image test result, or the like, or any combination thereof. In some embodiments, the database module 230 may perform the retrieval according to one or more indexes to improve retrieval efficiency.

In some embodiments, the database module 230 may perform an operation on one or more databases. Operations on the database may include creating, accessing, modifying, updating, or deleting one or more databases. Creating one or more databases may be creating or enabling one or more new databases for storage and/or retrieval of information. Accessing one or more databases may be accessing one or more created databases for storage and/or retrieval of information. Modifying one or more databases may be modifying or replacing information in one or more created databases. Updating one or more databases may be replacing or updating information in one or more created databases. Deleting one or more databases may be deleting information in one or more created databases. In some embodiments, the database module 230 may use one or more database languages, such as a data definition language, a data manipulation language, a data query language, a data control language, a transaction control language, or the like, or any combination thereof. In some embodiments, the image analysis system 100 may allow a user with appropriate access rights to access the database module 230. The access rights may include, for example, reading some or all information associated with the stored information, updating some or all information associated with the stored information, or the like, or any combination thereof. The access rights may be associated with a set of login information and linked to the login information. In some embodiments, the login information may be a user account or a login password that is input when the user logs in to the image analysis system 100. In some embodiments, the image analysis system 100 may provide one or more layers of access rights. In some embodiments, the first layer access rights may be a complete access to the stored information, for example, allowing the stored information to be received and updated; the second layer access rights may be a partial access to the stored information, for example, allowing some of the stored information to be received and updated; and the third layer access rights may be a minimal access to the stored information, for example, allowing some of the stored information to be received and updated. The update may include providing information that does not exist in the image analysis system 100, or modifying information existing in the image analysis system 100 using new information. In some embodiments, the login information may be associated with different access rights of the three layers.

It should be noted that the above description of the multi-modality image processing system 130 is for convenience of description only, and cannot limit the present disclosure within the scope of the illustrated embodiments. It should be understood by those skilled in the art that after understanding the principle of the system, each module may be arbitrarily combined, a subsystem may be connected with other modules, and various modifications and changes may be made in the form and detail of the application field of the above method and system without departing from the principle. For example, the database module 230 may be integrated in a storage device (e.g., the hard disk 182, the ROM 183, the random access storage (RAM) 185, a cloud storage, etc.). As another example, the visualization module 210 may be integrated in the I/O 184. As another example, the analysis module 220 may be integrated in the processor 181.

Figure 3:
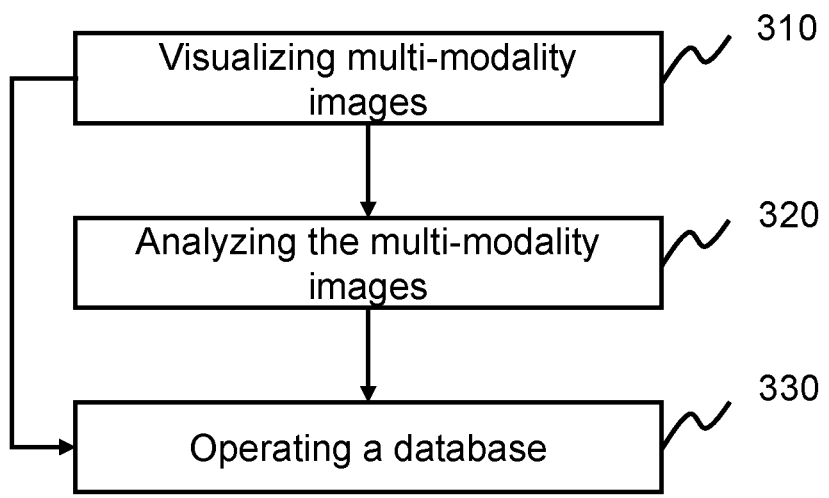
FIG. 3 is a flowchart illustrating an exemplary process for processing multi-modality images according to some embodiments of the present disclosure.

FIG. 3 is a flowchart illustrating an exemplary process for processing multi-modality images according to some embodiments of the present disclosure. In some embodiments, the multi-modality image processing system 130 may execute a process for processing multi-modality images. The process for processing multi-modality images may include 310 of visualizing multi-modality images, 320 of analyzing the multi-modality images, and 330 of operating a database.

Figure 5:
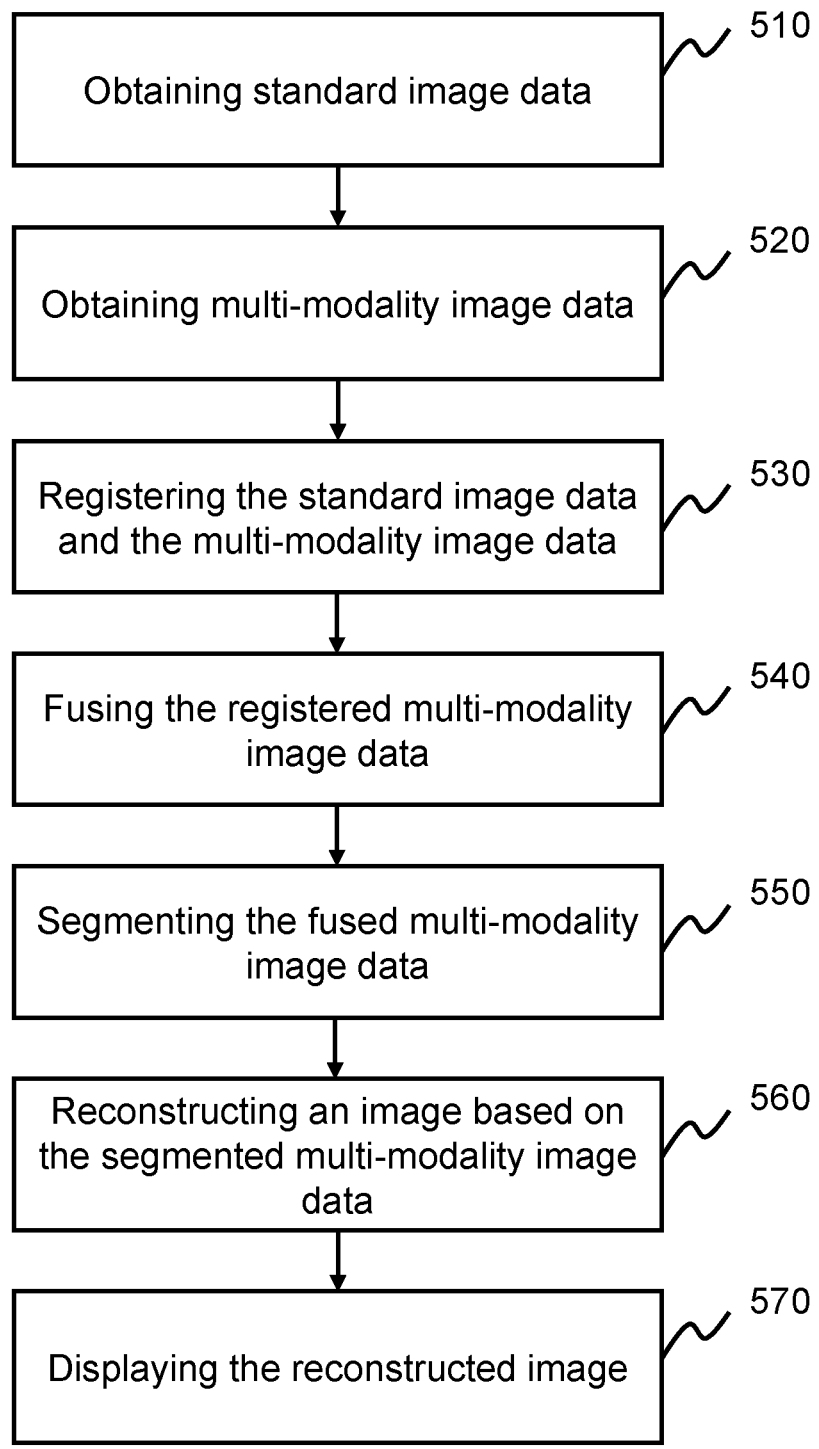
FIG. 5 is a flowchart illustrating an exemplary process for visualization according to some embodiments of the present disclosure.

In 310, multi-modality images may be visualized. In some embodiments, the visualization module 210 may execute operation 310. The visualization process of the multi-modality images may further include, as shown in FIG. 5, registering the multi-modality images, fusing the multi-modality images, segmenting the multi-modality images, reconstructing an image based on multi-modality image data obtained by the segmentation, and/or displaying the reconstructed image, or the like. In some embodiments, the multi-modality images may include images including one modality or a plurality of different modalities, for example, an MRI image, a CT image, an MRA image, an fMRI image, a PET image, a DTI/DTT image, a CT-PET image, an fMRI-DTI image, a TOF-MRI image, a TOF-MRA image, or the like, or any combination thereof.

Figure 7:
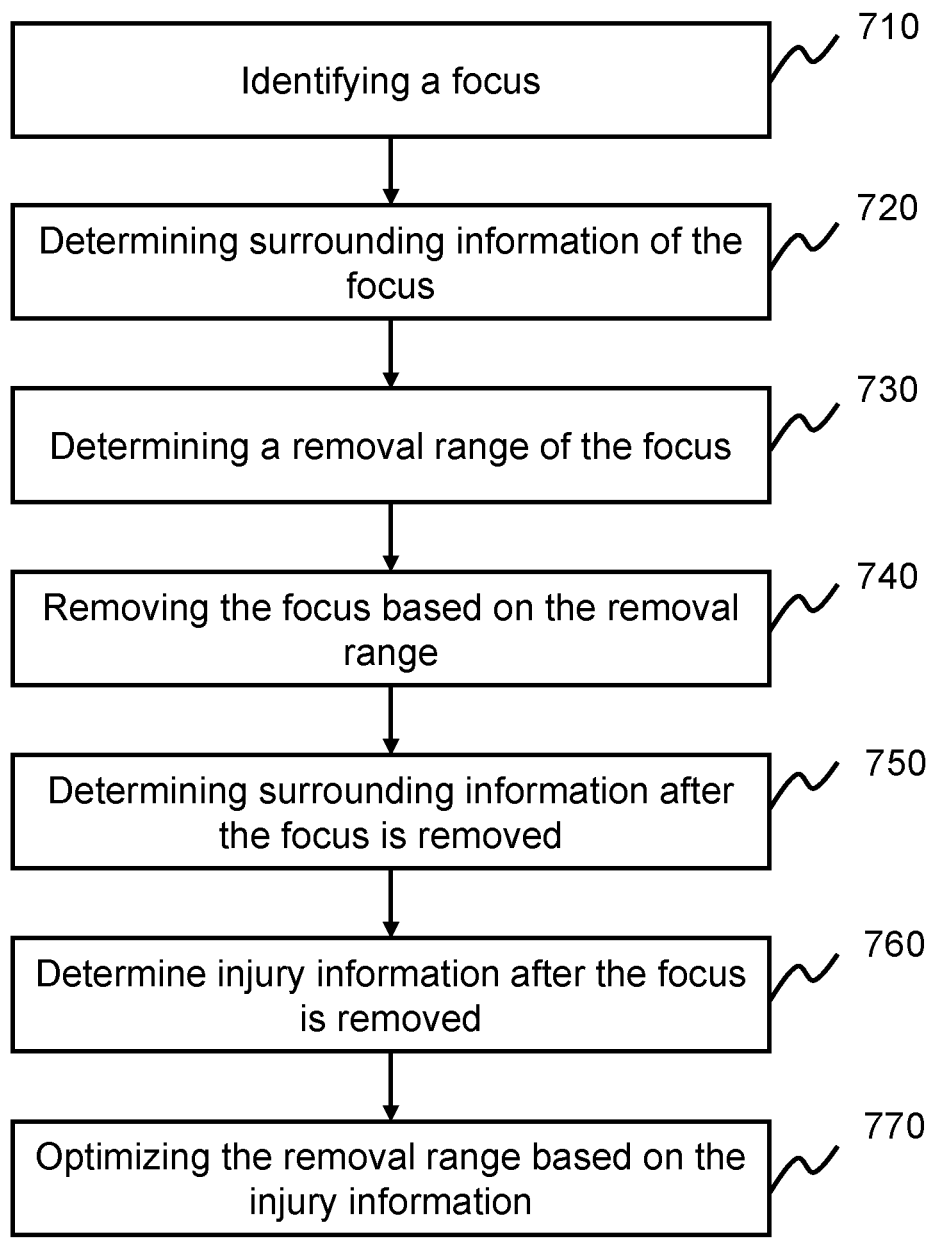
FIG. 7 is a flowchart illustrating an exemplary process for analyzing multi-modality images according to some embodiments of the present disclosure.

In 320, the multi-modality images may be analyzed. In some embodiments, in 320, analysis may be performed on the visual multi-modality images in 310. In some embodiments, the analysis module 220 may execute operation 320. In some embodiments, 320 may further include, as shown in FIG. 7, determining a location of a focus in the multi-modality images, determining surrounding information of a focus, determining a removal range of the focus, determining surrounding information after the focus is removed, determining injury information after the focus is removed, and/or optimizing the removal range, or the like. In some embodiments, a single modality image may be analyzed individually in 320. For example, in a brain CT image, 320 may determine information such as a relationship between brain tissue and a brain function, or the like. In some embodiments, comprehensive analysis may be performed on a reconstructed image in 320. For example, in a reconstructed image, 320 may determine an optimized removal range of the focus to guide a surgical operation.

In 330, a database may be operated. In some embodiments, the database module 230 may execute operation 330. In some embodiments, 330 may further include storing information in the database, and/or retrieving the information in the database, or the like. The information may be basic information of a patient corresponding to the multi-modality images, case information of the target object displayed on the multi-modality images, information related to the multi-modality images, or the like, or any combination thereof. In some embodiments, the information may be retrieved according to one or more methods. The method of retrieving information may include retrieval of a keyword based on one or more kinds of stored information, or automatic retrieval. In some embodiments, machine learning of the database information may be performed according to one or more machine learning algorithms to optimize the removal range of the focus or to provide an optimized surgery plan so as to provide a reference opinion for the physician.

It should be noted that the above description of the process for processing multi-modality images is merely a specific example and should not be considered as the only feasible implementation. It may be apparent to those skilled in the art that various modifications and changes may be made in the form and detail of the specific embodiment and steps of the multi-modality image processing process 130, and a number of simple deduction or replacement may be made without departing from the principles of the present disclosure after understanding the basic principles of processing the multi-modality images, a certain adjustment or combination is made to the order of an individual step without making creative efforts, but such modifications and changes are still within the scope of the above description. For example, 330 may be directly executed after the 310 is executed. As another example, 330 may be omitted. As still another example, 330 may be performed independently.

Figure 4:
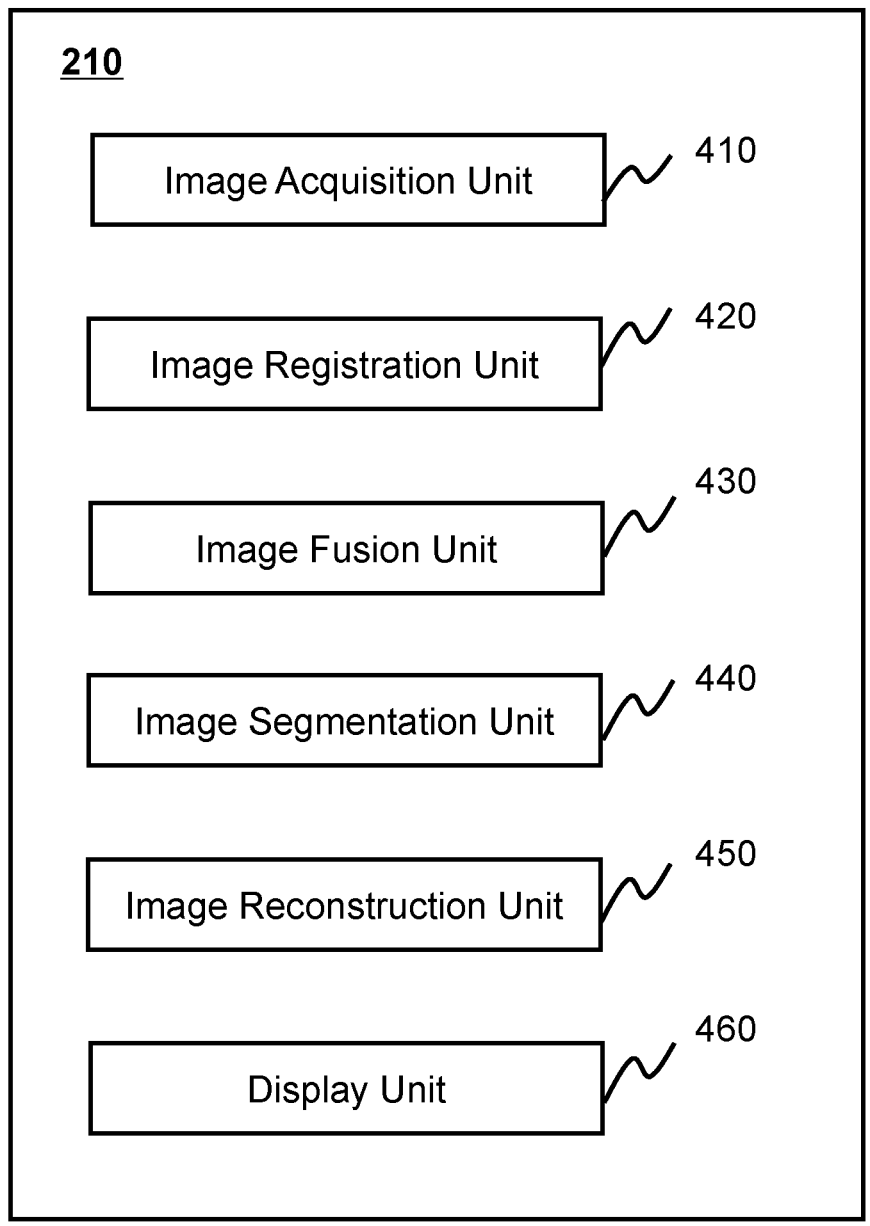
FIG. 4 is a schematic diagram illustrating an exemplary visualization module according to some embodiments of the present disclosure.

FIG. 4 is a schematic diagram illustrating an exemplary visualization module according to some embodiments of the present disclosure. The visualization module 210 may include an image acquisition unit 410, an image registration unit 420, an image fusion unit 430, an image segmentation unit 440, an image reconstruction unit 450, and a display unit 460. The units may be directly and/or indirectly connected to each other. It may be apparent that the visualization module 210 described in FIG. 4 may merely represent some embodiments of the present disclosure. For those of ordinary skill in the art, modifications, additions and deletions may be made without making creative efforts. For example, two units can be combined as one unit; alternatively, one unit may be segmented into two or more units.

The image acquisition unit 410 may acquire an image (and/or image data). The acquired image (and/or image data) may be directly acquired from the imaging device 110, the processor 181, the storage device (e.g., the hard disk 182, the ROM 183, the RAM 185, the cloud storage, etc.), the I/O 184, or acquired via the network 160. The target object displayed on the acquired image may be a human, an animal, or a portion thereof, for example, an organ, tissue, a lesion site (e.g., a tumor site), or the like, or any combination thereof. For example, the target object may be a head, a chest, an abdomen, a heart, a liver, an upper limb, a lower limb, a vertebra, a bone, a blood vessel, or the like, or any combination thereof. In some embodiments, the acquired image data may be two-dimensional image data and/or three-dimensional image data. In some embodiments, the acquired image data may be image data generated at different times, with different imaging devices, and/or in different conditions (e.g., weather, illuminance, scanning locations and angles, etc.). In some embodiments, the acquired image data may be image data including one modality, and/or image data including any combination of a plurality of different modalities. For example, the acquired image data may include an MRI image, a CT image, an MRA image, an fMRI image, a DTI image, a DTT image, an fMRI-DTI image, a TOF-MRI image, a TOF-MRA image, or the like, or any combination thereof. In some embodiments, the acquired image data may be standard image data, and/or image data including any combination of different modalities. In some embodiments, the acquired image data may be image data of a particular site scanned according to the inspection requirements, for example, a panoramic scan of the target object, blood vessels, nerve distribution, a functional region, tissue metabolic information of the target object, or the like, or any combination thereof. In some embodiments, the acquired image data may be original data of a brain image, processed brain image data, or parameters of brain image processing, or the like.

The image registration unit 420 may register two or more images. The two or more images may be images including the same modality, or images including different modalities. The two or more images may be images obtained at different times, with different imaging devices, and/or in different conditions (e.g., weather, illuminance, scanning locations and angles, etc.). Image registration may refer to performing a process of matching and superimposing two or more images. In some embodiments, the image registration unit 420 may use a spatial location of the target object as a basis for registration. For example, the registration may be performed based on the same or similar spatial location of the same anatomical point of the target object in two or more images. In some embodiments, the image registration unit 420 may match one or more anatomical points of the target object in two or more images, or points of interest (e.g., a point having diagnosis significance, a point closely related to the surgery plan) in the two or more images.

For images including different modalities, the image registration unit 420 may adopt the same or different image registration ways, for example, relative registration, and/or absolute registration. The relative registration may select an image as a reference image and register other images with the reference image. In some embodiments, coordinate systems of the reference image and the other images may be optional, for example, the coordinate systems of the reference image and the other images may be same or different. The absolute registration may first select a coordinate system and then transform the coordinate systems of the multi-modality images into the selected coordinate system to achieve unification of coordinate system. In some embodiments, the image registration unit 420 may geometrically correct the multi-modality images to achieve unification of coordinate system. In some embodiments, the geometric correction of the multi-modality images may be achieved based on one or more geometric transform polynomials. For example, a plurality of homonymy points that uniformly distribute in the multi-modality images may be determined, and then polynomial coefficients of the geometric transformation may be determined according to the homonymy points of the multi-modality images, so that geometric correction of an image is achieved through another image.

In some embodiments, the image registration unit 420 may use an image showing an anatomical structure (e.g., MRI-T1) as a reference image and register other images (e.g., DTI/DTT, CT/PET, MRI TOF, or the like, or any combination thereof) with the MRI-T1. In some embodiments, the image registration unit 420 may use standard image data as a reference image and register fMRI-BOLD image data with the standard image data.

The image registration unit 420 may perform image registration based on one or more image registration methods. In some embodiments, the image registration methods may be a point method (e.g., an anatomical landmark point), a curve method, a surface method (e.g., a surface profile method), a moment and principal axes method (e.g., a spatial coordinate alignment method), a cross-correlation method, an interactive information method, a sequential similarity detection algorithm (SSDA), an image method, a nonlinear variation method, or the like, or any combination thereof. In some embodiments, the image registration method may be a multi-resolution method based on maximum interactive information, a gray statistical method based on the maximum interactive information, a feature image registration method based on the surface profile, or the like, or any combination thereof. In some implementations, the image registration unit 420 may select one or more image registration methods for image registration. The selection of the image registration method may be automatic, semi-automatic or manual. For example, the image registration unit 420 may select an image registration method based on history of the multi-modality image registrations in the same category. As another example, the image registration unit 420 may perform manual intervention on a fully automatically or semi-automatically selected image registration method to achieve multi-modality image registration. As still another example, the user may manually select the image registration method through the I/O 184 or the remote terminal 170. As still another example, the user may perform parameter setting and adjustment on the image registration method that the image registration unit 420 automatically selects.

The image fusion unit 430 may fuse images. In some embodiments, the image fusion unit 430 may fuse two or more images after the registration. Image fusion may refer to extracting effective information in the multi-modality images that have the same target object, and combining the multi-modality images to generate an image, so as to improve spatial resolution and spectral resolution of image information. In some embodiments, the image fusion unit 430 may reflect effective information of the multi-modality images in the fused image. In some embodiments, the image fusion unit 430 may take advantageous of the multi-modality images to fuse a new image, in which a part or all of the information from the multi-modality images can be displayed.

The image fusion unit 430 may perform image fusion based on one or more image fusion algorithms. In some embodiments, the image fusion algorithms may include a luminance hue saturation (IHS) algorithm, a principal component analysis (PCA) method, a batch transform algorithm, a multiplicative algorithm, a wavelet transform method (e.g., three-dimensional wavelet transform method), or the like, or any combination thereof. In some embodiments, image fusion may be classified as decision-level fusion, feature-level fusion, and data-level fusion (pixel-level fusion) according to levels. The decision-level fusion may perform analysis, deduction, identification, and judgment using a large database and an expert decision system based on a cognitive model method, for example, only need to correlate data. The decision-level fusion may also be based on a number of other rules, for example, a Bayesian method, a D-S evidence method, a voting method, or the like. The feature-level fusion may fuse feature information (e.g., edge, shape, texture, region, etc.) of an image. The pixel-level fusion may directly process the data of one or more pixels of the obtained multi-modality images to obtain a fused image. The pixel-level fusion may perform image fusion based on one or more algorithms, for example, a spatial domain algorithm, and/or a transform domain algorithm, or the like. In some embodiments, the spatial domain algorithm may include a logic filtering method, a gray weighted average method, or a contrast modulation method, or the like. In some embodiments, the transform domain algorithm may include a pyramid decomposition fusion method, or a wavelet transform method. In some embodiments, the pixel-level fusion and the feature-level fusion may register and correlate information (e.g., original image data, an eigenvector, etc.) of multi-modality images, while decision-level fusion may correlate image data.

In some implementations, the image fusion unit 430 may select one or more image fusion methods for image fusion. The selection of the image fusion method may be automatic, semi-automatic or manual. The image fusion unit 430 may select an image fusion method based on history of the multi-modality image registrations in the same category. As another example, the user may manually select the image fusion method through the I/O 184 or the remote terminal 170. As still another example, the user may perform parameter setting or adjustment on the image fusion method that the image fusion unit 430 automatically selects.

The image segmentation unit 440 may segment images. In some embodiments, the image segmentation unit 440 may perform segmentation in a single modality image, or in the multi-modality images. In some embodiments, the image segmentation unit 440 may perform image segmentation before image registration and/or fusion, or perform image segmentation after image registration and/or fusion. The image segmentation process may be performed based on corresponding features of the pixel (or voxel) of an image. In some embodiments, the corresponding features of the pixel (or voxel) may include texture, gray, average gray, signal intensity, color saturation, contrast, luminance, or the like, or any combination thereof. In some embodiments, spatial location features of the pixel (or voxel) may also be used for the image segmentation process. In some embodiments, the image segmentation unit 440 may segment the multi-modality images by manual, automatic, or semi-automatic segmentation methods based on medical image characteristics of the target object. The segmented image may include an organ or tissue, a vascular structure, nerve fibers, a structural functional region of the target object, or the like, or any combination thereof. For example, the image segmentation unit 440 may segment a brain fMRI-BOLD image and obtain a brain tissue structure and a corresponding brain functional region. As another example, the image segmentation unit 440 may segment a brain fMRI-DTI/DTT image to obtain brain nerve fibers. As still another example, the image segmentation unit 440 may segment a brain TOF-MRI image to obtain blood vessels of the brain. In some embodiments, the image segmentation unit 440 may perform image segmentation based on one or more segmentation methods. For example, the image segmentation may be segmentation based on the gray threshold, a regional growth and split merge method, an edge segmentation method, a histogram method, segmentation based on a fuzzy theory (e.g. fuzzy threshold segmentation, fuzzy connectedness segmentation, fuzzy clustering segmentation, etc.), segmentation based on nerve network, segmentation based on mathematical morphology (e.g. a morphological watershed algorithm, etc.), or the like, or any combination thereof. In some embodiments, the image segmentation unit 440 may perform image segmentation based on the similarity of gray values among adjacent pixels and difference of gray values among different pixels in the fused image.

The image reconstruction unit 450 may reconstruct a three-dimensional and/or two-dimensional image. In some embodiments, the image reconstruction unit 450 may reconstruct an image based on the multi-modality image data to display the multi-modality information of the target object. In some embodiments, the image reconstruction unit 450 may reconstruct the image based on image data obtained by registration, fusion, and/or segmentation. In some embodiments, the image reconstruction unit 450 may establish one or more organ or tissue models, such as a vascular model, a segmentation model of tissue of an organ, a connection model of nerve fibers, a three-dimensional overall model of the target subject, or the like, or any combination thereof. In some embodiments, the image reconstruction unit 450 may perform image reconstruction based on one or more reconstruction techniques or methods. For example, the image reconstruction may be based on a surface model method, a voxel model method, or the like, or any combination thereof. The surface model method may include a contour reconstruction method, a voxel reconstruction method, a volume rendering (VR) method, a multi-planar reformation (MPR) method, a maximum intensity projection (MIP), or surface shadow display (SSD) method, or the like. The voxel model method may include a spatial domain method, a transform domain method, or the like. In some embodiments, the image reconstruction unit 450 may obtain a three-dimensional reconstructed image based on the segmented image data by using techniques such as visualization toolkit (VTK) or open scene graph (OSG) based on a three-dimensional reconstruction technique.

The display unit 460 may display an image. In some embodiments, the display unit 460 may display an image acquired by the image acquisition unit 410, an image registered by the image registration unit 420, an image fused by the image fusion unit 430, an image segmented by the image segmentation unit 440, an image reconstructed by the reconstruction unit 450, information generated by the analysis module 220, information obtained by the database module 230 through operating the database, and/or information in any process for processing the multi-modality images. In some embodiments, the display unit 460 may display the target object and surrounding tissue information in the reconstructed image, for example, a spatial anatomy structure of the target object, surrounding vascular tissue, nerve fibers, a structural functional region, and tissue metabolic conditions, or the like, or any combination thereof.

FIG. 5 is a flowchart illustrating an exemplary process for visualization according to some embodiments of the present disclosure. In some embodiments, the visualization module 210 may perform a visualization process. The visualization process may further include 510 of obtaining standard image data, 520 of obtaining multi-modality image data, 530 of registering the standard image data and the multi-modality image data, 540 of fusing the registered multi-modality image data, 550 of segmenting the fused multi-modality image data, 560 of reconstructing an image based on the segmented multi-modality image data, and 570 of displaying the reconstructed image, or the like.

In 510, standard image data may be obtained. In some embodiments, the image acquisition unit 410 may perform operation 510. In some embodiments, the standard image data may be an image displaying information relating to a target object, and may be referenced as a standard, for example, a standard lung map, a standard cardiac map, a standard brain map, or the like, or any combination thereof. In some embodiments, the standard image data may be directly obtained from a storage device (e.g., the hard disk 182, the ROM 183, the RAM 185, the cloud storage, etc.), the I/O 184, or obtained from an external data source. In some embodiments, the standard image data may be obtained from other standard image databases via the network 160.

In 520, multi-modality image data may be obtained. The image acquisition unit 410 may perform operation 520. In some embodiments, the multi-modality image data may be directly obtained from the imaging device 110, the processor 181, the storage device (e.g., the hard disk 182, the ROM 183, the RAM 185, the cloud storage, etc.), the I/O 184, or obtained from an external data source, or obtained via the network 160. The obtained multi-modality image data may be original image data, processed image data, or image processing parameters, or the like, or any combination thereof. In some embodiments, the multi-modality image data may relate to magnetic resonance imaging (MRI), functional magnetic resonance imaging blood oxygen level dependent (fMRI-BOLD), diffusion tensor imaging (DTI), diffusion tensor tractography (DTT), magnetic resonance angiography (MRA), computed tomography (CT), positron emission tomography (PET), single photon emission computed tomography (SPECT), time-of-flight magnetic resonance imaging (TOF-MRI), time-of-flight magnetic resonance angiography (TOF-MRA), magnetoencephalogram (MEG), ultrasonic scanning (US), transcranial magnetic stimulation magnetic resonance imaging (MR-MRI), MRI-T1, MRI-T2, fMRI-DTI, fMRI-DTT, CT-PET, CT-SPET, PET-MR, PET-US, SPECT-US, US-CT, US-MR, X-CT, X-PET, X-US, or the like, or any combination thereof. In some embodiments, for different target objects or imaging methods, the numbers of multi-modality images included in the multi-modality image data and modalities of the multi-modality image data may be different. For example, brain-related scan images may include MRI-T1, MRI-T2, fMRI-BOLD, fMRI-DTI, fMRI-DTT, CT-PET, or the like, or any combination thereof.

In 530, the multi-modality image data obtained in 520 and the standard image data obtained in 510 may be registered. In some embodiments, the multi-modality image data obtained in 520 may also be directly registered in 530, without being registered based on the standard image data. The image registration unit 420 may perform operation 530. In 530, the multi-modality image data and the standard image data may be registered using one or more of the image registration methods described above. In some embodiments, an image registration process may include extracting features of multi-modality images and a standard image to obtain feature points, finding matched feature point pairs in the multi-modality images and the standard image by a similarity measure, obtaining spatial coordinate transformation parameters of the multi-modality images and the standard image based on the matched feature point pairs, and performing image registration based on the spatial coordinate transformation parameters. In some embodiments, the registration of the multi-modality image data and the standard image data may be performed using MRI T1 as a reference image, other images (e.g., DTI/DTT, CT/PET, MRI TOF, or the like, or any combination thereof) may be registered with the MRI-T1. In some embodiments, the registration of the multi-modality image data with the standard image data may use the standard image data as a reference image and register the fMRI-BOLD image data with the standard image data. In some embodiments, coordinate systems adopted for MRI-T1, fMRI-BOLD image data, and/or standard image data may be optional. In some embodiments, an image generated based on registration of the fMRI-BOLD image data with the standard image data may be registered with MRI-T1 again. In some embodiments, the registration method of the multi-modality image data and the standard image data may be a multi-resolution method based on maximum interactive information, a gray statistical method based on maximum interactive information, a feature image registration method based on a surface profile, or the like, or any combination thereof.

In 540, the multi-modality image data registered in 530 may be fused. The image fusion unit 430 may perform operation 540. In 540, the multi-modality image data may be fused using one or more of the image fusion methods described above. In some embodiments, the fusion method of the multi-modality image data may include a logic filtering method, a gray weighted average method, a contrast modulation method, a pyramid decomposition fusion method, a wavelet transform method (e.g., a three dimensional wavelet transform method), a Bayesian method, a D-S evidence method, a voting method, or the like, or any combination thereof.

In 550, the multi-modality image data fused in 540 may be segmented. The image segmentation unit 440 may perform operation 550. In some embodiments, the segmentation of the multi-modality image data may obtain an organ or tissue, a vascular structure, nerve fibers, a functional region of the target object, or the like, or any combination thereof. For example, a brain tissue structure and a corresponding brain functional region may be obtained by the segmentation in a brain fMRI BOLD image; brain nerve fibers may obtained by the segmentation in a brain fMRI-DTI/DTT image; a vascular structure of the brain may be obtained by the segmentation in a brain TOF-MRI image.

In 560, an image may be reconstructed based on a result of the segmentation in 550. The image reconstruction unit 450 may perform operation 560. In some embodiments, the image reconstruction may reconstruct a three-dimensional model of the target object using a three-dimensional reconstruction technique to achieve three-dimensional modeling of the target object and the surrounding tissue based on information such as an organ or tissue, a vascular structure, nerve fibers, a functional region of the target object, or the like. In some embodiments, the image reconstruction performed in 560 may include a surface reconstruction of the target object, or a volume reconstruction of the target object. The surface reconstruction may form a three-dimensional surface data set based on the image data of the target object obtained through the segmentation, and perform three-dimensional surface reconstruction. The volume reconstruction may form a three-dimensional volume data set based on the image data of the target object through the segmentation, and perform three-dimensional volume reconstruction.

In 570, the reconstructed image in 560 may be displayed. In some embodiments, intermediate information and/or a result of any one of operation 510 to operation 560 may be displayed in 570. For example, the multi-modality images acquired in 520, a result of the registration in 530, a result of the fusion in 540, and/or a result of the segmentation in 550 may be displayed. The display unit 460 may perform operation 570. In some embodiments, 570 may display the target object and/or three-dimensional (and/or two-dimensional) surrounding information in the reconstructed image. For example, 570 may display a spatial anatomy structure, surrounding vascular tissue, nerve fibers, a functional region of the target object, or the like, or any combination thereof.

It should be noted that the above description of the visualization module and the visualization process is merely a specific example and should not be considered as the only feasible implementation. Each of the above units may be implemented by one or more parts, and a function of each unit is not limited thereto. Each of the above units may be selected to be added or deleted depending on a particular implementation scenario or as necessary. It may be apparent to those skilled in the art that various modifications and changes may be made in the form and detail of the specific embodiment and steps of the image visualization, and a number of simple deduction or replacement may be made without departing from the principles of the present disclosure after understanding the basic principles of the image visualization, a certain adjustment or combination is made to the order of the units and/or the visualization steps without making creative efforts, but such modifications and changes are still within the scope of the above description. For example, 510 and 520 may be combined as a single operation. As another example, 510 and 520 may be executed in turn, simultaneously, or alternately. As still another example, 550 and 560 may be combined as a single operation. As still another example, 550 and 560 may be executed in turn, simultaneously, or alternately. As still another example, operation 570 for display may be added before or after any of the operations between 510 and 560.

Figure 6:
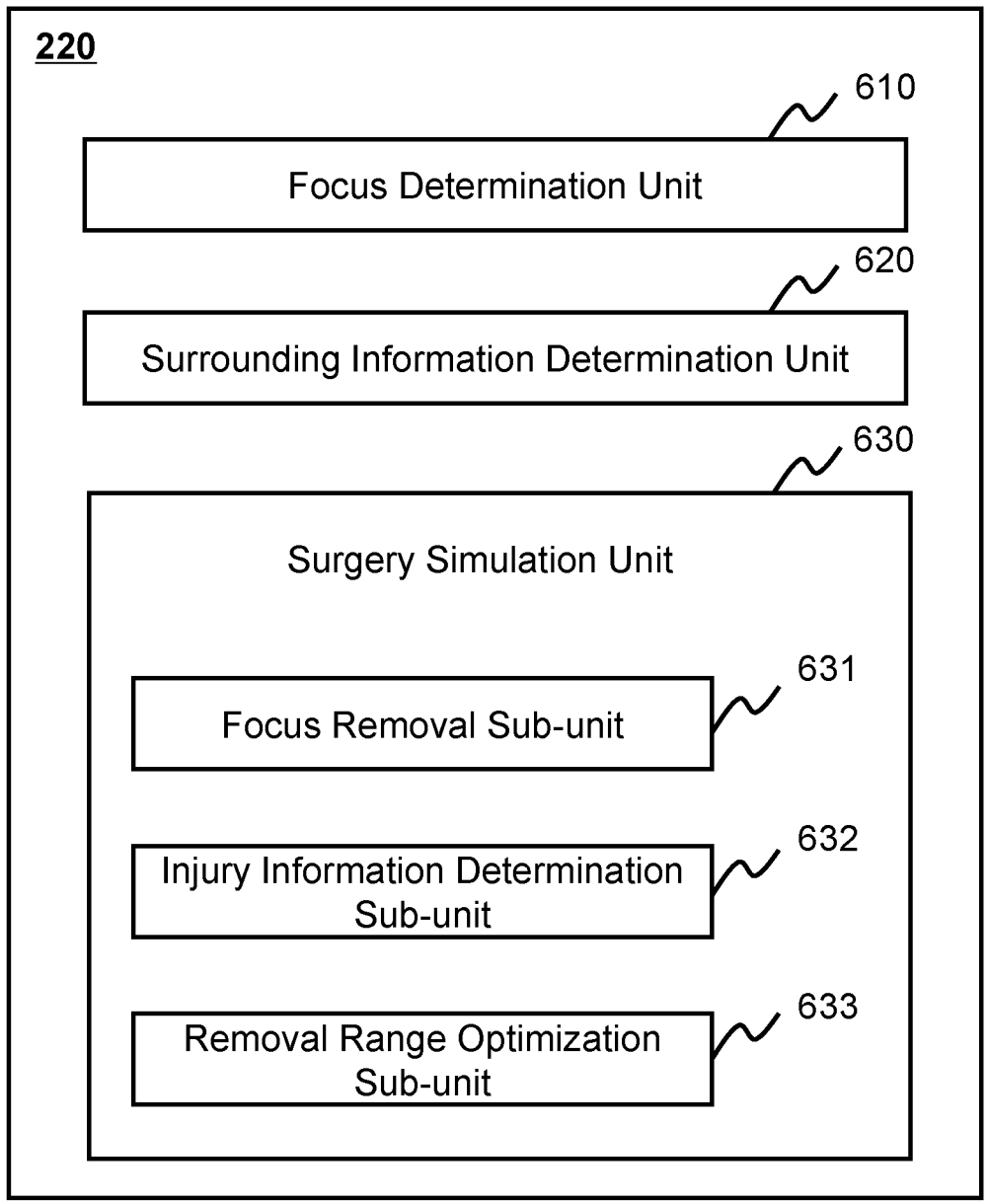
FIG. 6 is a schematic diagram illustrating an exemplary analysis module according to some embodiments of the present disclosure.

FIG. 6 is a schematic diagram illustrating an exemplary analysis module according to some embodiments of the present disclosure. The analysis module 220 may include a focus determination unit 610, a surrounding information determination unit 620, and a surgery simulation unit 630. The units may be directly (and/or indirectly) connected to each other. It may be apparent that the analysis module 220 in FIG. 6 is merely a specific example, and for those skilled in the art, modification, addition and deletion may be made without making creative efforts. For example, two units may be combined as one unit; alternatively, one unit may be segmented into two or more units.

The focus determination unit 610 may determine focus information in an image. The image may include at least one of the multi-modality images acquired by the image acquisition unit 410, an image registered by the image registration unit 420, an image fused by the image fusion unit 430, an image segmented by the image segmentation unit 440, and/or an image reconstructed by the reconstruction unit 450. The focus information may include information such as a location, a shape, a diameter, a volume of a focus, and/or a count of focuses. In some embodiments, the focus may be a tumor, bleeding, calcification, infarction, inflammation, pathogen infection, tissue congenital abnormality, or the like, or any combination thereof. In some embodiments, the focus may be measured at different angles in the reconstructed image or in any sagittal, coronal, and axial cross-section to determine the location, shape, diameter, volume, count of the focus, or the like, or any combination thereof. In some embodiments, the focus information may be manually determined in the two-dimensional and/or three-dimensional reconstructed image by the user through the I/O 184, and/or the remote terminal 170, or be automatically determined in the two-dimensional and/or three-dimensional reconstructed image by the focus determination unit 610 through one or more algorithms. For example, the algorithms may include a regional growth method based on a gray value, an algorithm based on a threshold value, or the like. In some embodiments, the focus information may be determined using a computer-aided diagnostic system (CAD) in a two-dimensional and/or three-dimensional reconstructed image. The computer-aided diagnostic system (CAD) may be integrated in the focus determination unit 610 or other modules and/or units of the multi-modality image processing system 130. In some embodiments, the focus information may be determined by the focus determination unit 610 by segmenting the reconstructed image through one or more models (e.g., a human structural model, an image pixel, or a gray value distribution model, etc.).

The surrounding information determination unit 620 may determine surrounding information of the focus. In some embodiments, the surrounding information of the focus may be information relating to a blood vessel surrounding the focus, information relating to a nerve surrounding the focus, information relating to an organ or tissue surrounding the focus, or any combination thereof. For example, the surrounding information of the focus may include a name, a count, a branching direction, and a blood flow rate of blood vessels that the focus passes through, a count and a connection of fibers that are affected by the focus, a name and a volume ratio of a functional region that is covered by the focus, metabolic information relating to tissue surrounding the focus, or the like, or any combination thereof. In some embodiments, surrounding information after the focus is removed may include information relating to a blood vessel surrounding the focus after the focus is removed, information relating to a nerve surrounding the focus after the focus is removed, information relating to an organ or tissue surrounding the focus after the focus is removed, or the like, or any combination thereof. The surrounding information after the focus is removed may include a name and/or a volume ratio of a surrounding remaining functional region after the focus is removed, a name, an amount, a branching direction, and a blood flow rate of the blood vessel surrounding the focus after the focus is removed, a count and a connection of the fiber surrounding the focus after the focus is removed, or the like, or any combination thereof. In some embodiments, the surrounding information determination unit 620 may determine the surrounding information based on one or more algorithms. For example, determination of the surrounding information may be based on a regional growth algorithm, edge detection, or the like, or any combination thereof.

The surgery simulation unit 630 may simulate a surgery. The process of simulating a surgery may include, as shown in FIG. 7, simulation of designing a surgery plan, a surgery simulation, simulation of result analysis, risk and post-operative analysis based on the simulation result. In some embodiments, the surgery simulation unit 630 may include a focus removal sub-unit 631, an injury information determination sub-unit 632, and a removal range optimization sub-unit 633.

The focus removal sub-unit 631 may determine focus removal information and/or remove the focus. The focus removal information may include information relating to a removal range, a removal volume, a removal order, a removal way, and a removal duration of the focus, an instrument used for removal of the focus, or other information related to removal of the focus (e.g., anesthesia, extracorporeal circulation, cannula, etc.), or any combination thereof. In some embodiments, a removal range of the focus may be the focus, or a range that is larger than the focus and includes the focus. The larger range may have the same or similar profile as the focus, or other profiles. The larger range may be 1%, 3%, 5%, 10%, 50% or any other number greater than the area and/or volume of the focus. In some embodiments, the focus removal sub-unit 631 may determine a removal range of the focus based on the surrounding information. In some embodiments, the removal range of the focus may be determined based on the surrounding information of the focus, such as a name, a count, a branching direction, and a blood flow rate of blood vessels that the focus passes through, a count and a connection of fibers that are affected by the focus, a name and a volume ratio of a functional region that is covered by the focus, and metabolic information relating to tissue surrounding the focus, to avoid or reduce an injury to the surrounding blood vessels, nerves, and organs. In some embodiments, removal of the focus may be removal of one or more pixels (or voxels) within the determined removal range.

In some embodiments, the focus removal sub-unit 631 may allow the user to participate in the removal of the focus. For example, the focus removal sub-unit 631 may receive an instruction from the remote terminal 170 and/or the I/O 184, which may be input by the user, and the focus removal sub-unit 631 may remove the focus according to the instruction. In this way, the user may select a removal range of the focus through the remote terminal 170 and/or the I/O 184 and remove the focus, thereby achieving manual or semi-automatic removal of the focus. In some embodiments, the focus removal sub-unit 631 may automatically remove the focus according to one or more algorithms. In some embodiments, the removal range of the focus may be determined by a user for manual intervention on the basis of a removal range of focus that is automatically determined based on one or more algorithms. In some embodiments, ways of removal may be removal based on one or more spatial planes. For example, the focus removal sub-unit 631 may remove the focus based on a two-dimensional plane, a three-dimension object, or the like, or any combination thereof.

The injury information determination sub-unit 632 may determine predicted injury information after the focus is removed. In some embodiments, the injury information may be predicted injury information relating to a blood vessel after the focus is removed, predicted injury information relating to nerves after the focus is removed, and/or predicted injury information relating to an organ or tissue after the focus is removed. In some embodiments, the injury information may include a predicted case indicating whether a vascular structure that is affected by the focus after the focus is removed may cause tissue ischemia or blood stasis, a predicted case indicating whether rupture or absence of nerve fibers surrounding the focus after the focus is removed may cause dysfunction, a predicted case indicating whether organs or tissue surrounding the focus may be injured or dysfunctional after the focus is removed, or the like, or any combination thereof.

In some embodiments, the injury information determination sub-unit 632 may determine the predicted injury information by comparing the surrounding information of the focus with the predicted surrounding information after the focus is removed. For example, the injury information determination sub-unit 632 may determine whether the removal of the focus will cause rupture or reduction of the nerve fibers by comparing a count and a connection of nerve fibers surrounding the focus with a count and a connection of nerve fibers after the focus is removed, thereby determining whether dysfunction will occur. In some embodiments, the injury information determination sub-unit 632 may determine one or more kinds of the injury information, for example, a count of injured blood vessels, a count of injured nerves, an injured area or volume of a functional region, or the like. In some embodiments, the injury information determination sub-unit 632 may determine blood vessels surrounding the focus, nerve fibers surrounding the focus, and a functional region surrounding the focus by one or more criteria so as to determine one or more kinds of the injury information. For example, it is possible to determine whether the blood vessels surrounding the focus are injured based on integrity of the blood vessels surrounding the focus (e.g., 90%, 80%, 70%, or other proportions) and a blood flow rate (e.g., stenosis or malformation of the blood vessels surrounding the focus, etc.). As another example, it is possible to determine whether nerve fibers are ruptured based on the count and the connection of nerve fibers surrounding the focus. As still another example, it is possible to determine whether a functional region is injured based on the remaining area or volume (e.g., 90%, 80%, 70%, or other proportions) of the functional region surrounding the focus. In some embodiments, the injury information determination sub-unit 632 may determine comprehensive information of two or more kinds of injury information. For example, the injury information determination sub-unit 632 may assign different weights to different injury information, thereby determining weight values of the two or more kinds of the injury information and using the weighting values as evaluation indices of the injury information. In some embodiments, the injury information determination sub-unit 632 may predict injury information of the surrounding tissue after the focus is removed for guiding a surgery plan or simulating a surgery process.

Figure 8:
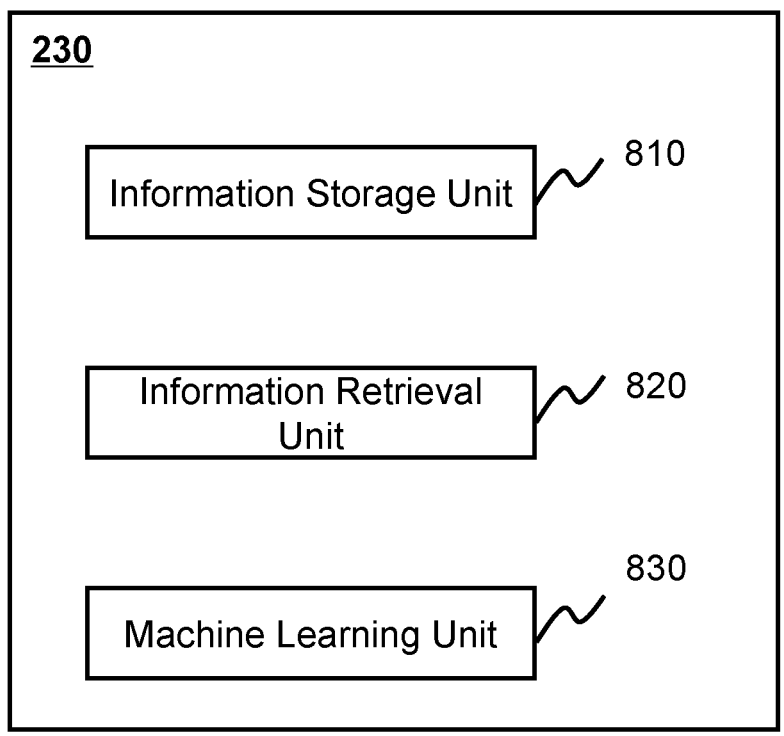
FIG. 8 is a schematic diagram illustrating an exemplary database module according to some embodiments of the present disclosure.

The removal range optimization sub-unit 633 may optimize the removal range of the focus. The optimizing the removal range of the focus may be performed based on one or more constraint conditions. The constraint conditions may include avoiding to injury important fibers, important blood vessels, important functional regions, important organs, important tissue, or the like, or any combination thereof. For example, the removal range optimization sub-unit 633 may designate a certain blood vessel or nerve (e.g., internal carotid, optic nerve, etc.) and prevent the certain blood vessel or nerve from being injured according to the request of a user. Then, the removal range optimization sub-unit 633 may avoid the blood vessel or nerve in the process of optimizing the removal range of the focus. In some embodiments, the removal range optimization sub-unit 633 may determine surgery simulating information such as the removal range, the surrounding information after the focus is removed, and the injury information by one or more optimizations. In some embodiments, the removal range optimization sub-unit 633 may optimize the removal range based on one or more standards. For example, the removal range optimization sub-unit 633 may use a standard of injuring vessels as few as possible, a standard of injuring a minimum area or volume of a functional region, or a standard of resulting in a minimum comprehensive effect of two or more injuries to the surrounding, or the like. In some embodiments, the removal range optimization sub-unit 633 may optimize the removal range based on the predicted injury information. In some embodiments, the removal range optimization sub-unit 633 may optimize the removal range based on a machine learning algorithm in the database module 230. FIG. 8 is a schematic diagram illustrating an exemplary database module according to some embodiments of the present disclosure. In some embodiments, the optimized removal range may be used for instructing a user to perform a surgery plan and/or making an optimal surgery plan.

FIG. 7 is a flowchart illustrating an exemplary process for analyzing multi-modality images according to some embodiments of the present disclosure. In some embodiments, the analysis module 220 may perform an analysis procedure. The analysis procedure may include 710 of identifying a focus, 720 of determining surrounding information of the focus, 730 of determining a removal range of the focus, 740 of removing the focus based on the removal range, 750 of determining surrounding information after the focus is removed, 760 of determine injury information after the focus is removed, and 770 of optimizing the removal range based on the injury information.

In 710, a focus may be identified based on the multi-modality images. In some embodiments, the focus may be identified based on the reconstructed image generated in 560. In some embodiments, the focus determination unit 610 may perform operation 710. In some embodiments, the focus may be determined automatically, semi-automatically or manually. For example, the user may manually outline the focus location, focus shape, focus diameter, focus volume, focus number, or the like, or any combination thereof, in the two-dimensional and/or three-dimensional reconstructed image by the I/O 184 or the remote terminal 170. As another example, the focus determination unit 610 may automatically identify the focus location, focus shape, focus diameter, focus volume, focus number, or the like, or any combination thereof, in the two-dimensional and/or three-dimensional reconstructed image by one or more algorithms. As still another example, the user may change or adjust the focus that is identified automatically.

In 720, surrounding information of the focus may be determined. In some embodiments, the surrounding information determination unit 620 may perform operation 720. In some embodiments, the determining the surrounding information of the focus may include determining information relating to a blood vessel surrounding the focus, information relating to a nerve surrounding the focus, information relating to tissue or an organ surrounding the focus, or the like, or any combination thereof, based on information relating to the focus location, focus shape, focus diameter, focus volume, or focus number determined in 710. In some embodiments, the surrounding information of the focus may include a name, a count, a branching direction, and a blood flow rate of blood vessels that the focus passes through, a count and a connection of fibers that are affected by the focus, a name and a volume ratio of a functional region that is covered by the focus, and metabolic information relating to tissue surrounding the focus, or the like, or any combination thereof.

In 730, a removal range of the focus may be determined. In some embodiments, the focus removal sub-unit 631 may perform operation 730. In some embodiments, the removal range may be determined in a way of expanding a focus margin. In some embodiments, the removal range may be the focus, or a range that is larger than the focus and includes the focus. In some embodiments, according to the surrounding information of the focus determined in 720, the removal range may be determined using a standard of avoiding or reducing an injury on the blood vessel surrounding the focus, the nerve surrounding the focus, the organ surrounding the focus, the tissue surrounding the focus, or the like.

In 740, the focus may be removed based on the removal range determined in 730. In some embodiments, the focus removal sub-unit 631 may perform operation 740. In some embodiments, the focus may be removed manually by a user through the I/O 184 or the remote terminal 170, or the focus may be automatically identified and removed by the focus removal sub-unit 631 according to one or more algorithms. In some embodiments, the focus removal may be based on removal of one or more spatial planes.

In 750, surrounding information after the focus is removed in 740 may be determined. In some embodiments, the surrounding information determination unit 620 may perform operation 750. The surrounding information after the focus is removed may be information relating to a blood vessel surrounding the focus after the focus is removed, information relating to a nerve surrounding the focus after the focus is removed, information relating to tissue or an organ surrounding the focus after the focus is removed, or the like, or any combination thereof.

In 760, injury information after the focus is removed in 740 may be determined. In some embodiments, the injury information determination sub-unit 620 may perform operation 760. In some embodiments, the injury information may be determined by comparing and analyzing the surrounding information before and after the focus is removed (e.g., comparing information determined in 750 and information determined in 720). In some embodiments, whether the blood vessels surrounding the focus are injured and/or an injury degree after the focus is removed may be determined by comparing and analyzing information relating to a name, a count, a branching direction, and a blood flow rate of blood vessels surrounding the focus before and after the focus is removed. In some embodiments, whether the fibers surrounding the focus are injured and/or an injury degree after the focus is removed may be determined by comparing and analyzing information relating to a count and a connection of the fibers surrounding the focus before and after the focus is removed. In some embodiments, whether the tissue or organ surrounding the focus is injured and/or an injury degree after the focus is removed may be determined by comparing and analyzing metabolic information relating to the organ or tissue surrounding the focus before and after the focus is removed.

In 770, the removal range of the focus may be optimized based on the injury information determined in 760. In some embodiments, the removal range optimization sub-unit 633 may perform operation 770. In some embodiments, the removal range determined in 730 may be optimized according to the injury information determined in 760. For example, a region in the removal range that causes a serious injury to the surrounding or a region in the expanded removal range that causes a lighter injury to the surrounding may be removed. In some embodiments, the optimizing the removal range of the focus may include repeating 730, 740, 750, and 760 one or more times. A more satisfactory removal range to the user may be determined by comparing and analyzing the injury information determined after the focus removal of one or more times, so as to assist to make a surgery plan for instructing an actual surgery operation. In some embodiments, the optimized removal range may be a best or better surgery removal result.

It should be noted that the above description of the analysis procedure is merely a specific example and should not be considered as the only feasible implementation. It may be apparent to those skilled in the art that various modifications and changes may be made in the form and detail of the specific embodiment and steps of the analysis process, and a number of simple deduction or replacement may be made without departing from the principles of the present disclosure after understanding the basic principles of the analysis process, a certain adjustment or combination is made to the order of an individual step without making creative efforts, but such modifications and changes are still within the scope of the above description. In some embodiments, 730 and 740 may be combined as one operation. In some embodiments, after 760 is performed, the analysis procedure may return to 730 to perform another determination of the removal range of the focus. In some embodiments, 750 and 760 may performed at the same time, or may be combined as one operation. In some embodiments, one or more operations may be added to the procedure, or deleted from the procedure. For example, a comparison operation between the injury information and a threshold may be added after 760. In some embodiments, the injury information determination sub-unit 632 or the removal range optimization sub-unit 633 may perform the comparison operation. As another example, an information storage operation may be added before or after any operation between 710 and 770, and information may be stored in the storage device (e.g., the hard disk 182, the ROM 183, the RAM 185, the cloud storage, etc.) or stored in the database module 230.

FIG. 8 is a schematic diagram illustrating an exemplary database module according to some embodiments of the present disclosure. The database module 230 may include an information storage unit 810, an information retrieval unit 820, and a machine learning unit 830. The shown units may be directly and/or indirectly connected with each other. It may be apparent that the above description of the database module 230 in FIG. 8 represents some embodiments of the disclosure, and to those skilled in the art various alternations, addition and deletion may be made according to the description of the database module without making creative efforts. For example, two units may be combined as one unit, or one unit may be segmented into two or more units.

The information storage unit 810 may store information. The information storage unit 810 may include one or more databases, for example, a universal database, a private database, or the like, or any combination thereof. In some embodiments, the universal database may be a Microsoft Office relational database (Microsoft office Access), a Sturctured Query Language (SQL) Server database, a MySQL database, an Oracle Database, a Sybase database, a Visual Foxpro (VF) database, an DB2 database, or the like, or any combination thereof. In some embodiments, the private database may be a database developed for storing information of certain type, for example, Apsara database (DB) for Remote Data Service (RDS). The information storied in the information storage unit 810 may be basic information of a patient corresponding to multi-modality images, case information of a target object shown on the multi-modality images, other related information, or the like, or any combination thereof. In some embodiments, the basic information may include a patient name, a patient gender, a patient age, a patient medical history, biochemistry examinations information of the patient, or the like, or any combination thereof. In some embodiments, the case information may include information relating to images, an image examination result, a system analysis result, a surgery plan, post-surgery recovery, or the like, or any combination thereof. In some embodiments, the related information may include a generation time of the multi-modality images, a generation time of an examination result of the multi-modality images, a system analysis time of the multi-modality images, a surgery operation time of the target object in the multi-modality images, or the like, or any combination thereof. In some embodiments, the information storage unit 810 may receive data and/or instructions from the processor 181, the storage device (e.g., the hard disk 182, the ROM 183, the RAM 185, the cloud storage, etc.), the I/O 184, the remote terminal 170, or other modules or units in the multi-modality image processing system 130, so as to store, change or delete information.

The information retrieval unit 820 may retrieval information. In some embodiments, the information retrieval unit 820 may retrieval information stored in the information storage unit 810. The retrieved information may be the case information of the target object shown on the multi-modality images or the basic information of the patient corresponding to the multi-modality images. In some embodiments, the information retrieval unit 820 may retrieval same information by one or more retrieval modes. In some embodiments, the information retrieval unit 820 may retrieve key words based on one or more types of the basic information of the patient corresponding to the multi-modality images, and the retrieval result may include the basic information of the patient and/or the case information of the target object shown on the multi-modality images. In some embodiments, the information retrieval unit 820 may perform retrieving based on one or more types of the case information of the target object shown on the multi-modality images, and the retrieval result may include the case information of the target object shown on the multi-modality images and/or the basic information of the patient corresponding to the multi-modality images. In some embodiments, the information retrieval unit 820 may retrieval the case information according to the basic information, or retrieval the basic information according to the case information.

In some embodiments, the information retrieval may include performing manual key word retrieval by a user through the I/O 184 or the remote terminal 170. In some embodiments, the information retrieval unit 820 may provide a smart retrieval function to retrieve case information similar to the case information of the multi-modality images. The similar case information may include a similar patient medical history, a similar focus location, a similar image examination result, a similar image modality, a similar surgery plan, or the like, or any combination thereof. In some embodiments, the multi-modality image processing system 130 may perform corresponding surgery plan design or improvement according to the similar case retrieved by the information retrieval unit 820. In some embodiments, the information retrieval unit 820 may display the retrieval result on the I/O 184 or the remote terminal 170, or the retrieval result may be transmitted to one or more users for further analysis via the network 160.

In some embodiments, the information retrieval unit 820 may perform information retrieval based on one or more algorithms. In some embodiments, the information retrieval unit 820 may retrieve information according to one or more indexes so as to improve the retrieval efficiency. For example, the information retrieval unit 820 may performing retrieving according to a word index and/or a character index. The word index may be a retrieval algorithm using a word as an index unit. The word index is difficult in a word segmenting algorithm, so that techniques of artificial intelligent analysis and context determination are introduced to improve the accuracy of the word index. The character index is a retrieval algorithm using a single Chinese character as an index unit.

The machine learning unit 830 may perform machine learning based on the information stored in the information storage unit 810. For example, according to the basic information of the patient corresponding to the multi-modality images, the case information of the target object shown on the multi-modality images, and the related information of the multi-modality images stored in the information storage unit 810, new data or knowledge may be obtained from one or more data using a machine learning algorithm. In some embodiments, the machine learning algorithm may be a decision tree algorithm, a K-means algorithm, a support vector machine (SVM) algorithm, an expectation maximization algorithm, an AdaBoost algorithm, an association rules (Apriori) algorithm, a K-nearest neighbor (KNN) algorithm, a naive Bayes algorithm, a neurotic network algorithm, a classification or regression tree algorithm, or the like, or any combination thereof.

In some embodiments, the machine learning unit 830 may adopt one or more machine learning algorithms describe above to perform learning based on one or more types of the case information of the target object shown on the multi-modality images. The machine learning unit 830 may optimize functions of one or more algorithms in the processing procedure and/or analysis procedure of the multi-modality images by learning one or more times, for example, a calculating method of the injury information after the focus is removed, a determination algorithm of the removal range, or the like, or any combination thereof. In some embodiments, the machine learning unit 830 may optimize the removal range of the focus based on surgery plans of a plurality of patients and post-surgery recovery information of the patients in combination with the surrounding information shown on the multi-modality images, the injury information after the focus is removed, or the like, so as to provide advisory opinions and/or plans for segmentation of a focus on other multi-modality images later. For example, for a brain tumor, the machine learning unit 830 may perform learning according to the case information of a plurality of samples of patients suffering a brain tumor at the same or similar location, and optimize or improve a determination algorithm of a removal range of the brain tumor by the learning. In some embodiments, the multi-modality image processing system 130 may have a diagnosis and/or treatment level up to, close to or higher than an expert doctor based on the learning of the machine learning unit 830. In some embodiments, the machine learning unit 830 may optimize and/or decrease individual difference of the processing results of the multi-modality images based on the K-nearest neighbor (KNN) algorithm, so as to avoid or reduce the injury to the patient in the actual surgery operation.

Figure 9:
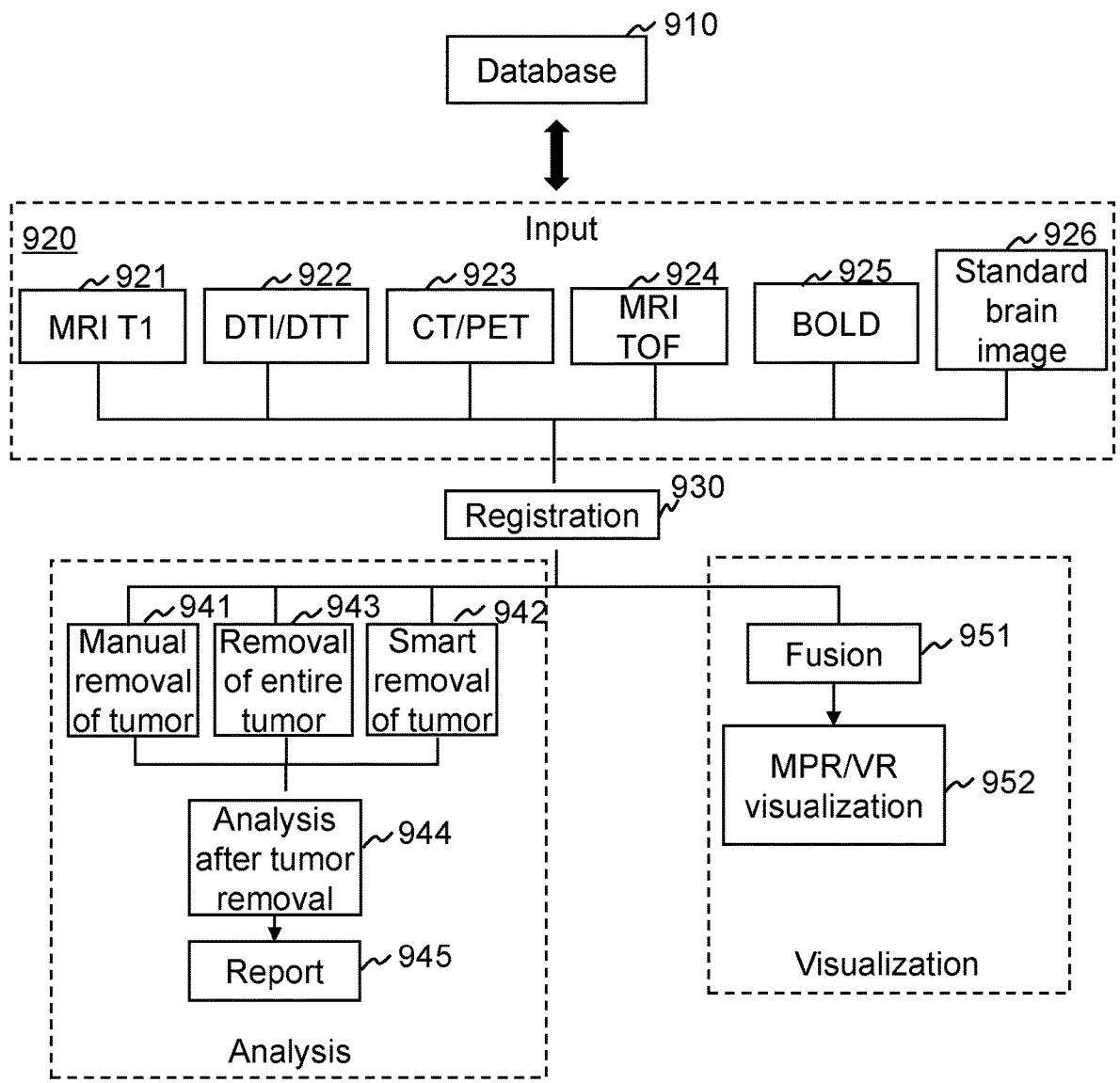
FIG. 9 is a schematic diagram illustrating an embodiment of a multi-modality image processing system according to some embodiments of the present disclosure.

FIG. 9 is a schematic diagram illustrating an embodiment of a multi-modality image processing system according to some embodiments of the present disclosure. The multi-modality image processing system 130 may acquire multi-modality brain image data from a database 910, obtain a visual brain image based on the data, perform analysis on the data, and generate an analysis report 945. The database 910 may be a database in the database module 230, a database in a local storage device (e.g., the hard disk 182, the ROM 183, the RAM 185, etc.), or a remote database in an external data source (e.g., a cloud storage, etc.).

The brain image data acquired from the database 910 by the multi-modality image processing system 130 may include static image data, video image data, two-dimensional image data, three-dimensional image data, or the like, or any combination thereof, for example, multi-modality image data such as MRI-T1image data 921, DTI/DTT image data 922, CT/PET image data 923, MRI TOF image data 924, and fMRI-BOLD image data 925. The acquired brain image data may further include ultrasound contrast data (e.g., a B-mode ultrasonic image), CT, SPECT, MEG, TMS-MRI, MRI-T2 data, CT-PET data, CT-SPET data, or the like, or any combination thereof. The data acquired from the database 910 by the multi-modality image processing system 130 may further include standard brain image data 926. In some embodiments, the multi-modality image processing system 130 may also acquire the brain image data from other device. For example, the multi-modality image processing system 130 may directly acquire the MRI-T1 image data 921 from a MRI imaging device, and directly acquire the MRI TOF image data 924 from another MRI imaging device.

In some embodiments, the MRI-T1 image data 921, the DTI/DTT image data 922, the CT/PET image data 923, the MRI TOF image data 924, the fMRI-BOLD image data 925, and/or the standard brain image data 926 may be acquired from the database 910 at the same time or at different times. For example, the MRI-T1image data 921, the DTI/DTT image data 922, the CT/PET image data 923, the MRI TOF image data 924, and the fMRI-BOLD image data 925 may be first acquired from the database 910, and the standard brain image data 926 may be acquired from the database 910 in the process for processing or analyzing the image data.

In operation 930 of image registration, the visualization module 210 may perform registration to the MRI-T1image data 921, the DTI/DTT image data 922, the CT/PET image data 923, the MRI TOF image data 924, the fMRI-BOLD image data 925, and the standard brain image data 926, and obtain a registration result. In some embodiments, the MRI-T1image data 921 may be used as a reference image, and registration of the DTI/DTT image data 922, the CT/PET image data 923, and the MRI TOF image data 924 may be separately performed based on the MRI-T1image data 921. In some embodiments, the standard brain image data 926 may be used as a reference image, and registration of the fMRI-BOLD image data 925 may be performed based on the standard brain image data 926. In some embodiments, after the registration is performed based on the standard brain image data 926, the registration of the fMRI-BOLD image data 925 may be performed based on the MRI-T1image data 921 again. The registration technique adopted in operation 930 of image registration may include a point method (e.g., anatomical landmark points), a curve method, a surface method (e.g., surface profile method), a moment and principal axes method (e.g., space coordinates alignment method), a cross-correlation method, an interaction information method, a sequential similarity detection algorithms, an image method, a nonlinear variation method, or the like, or any combination thereof. For example, anatomical structure information of the brain (e.g., location information of a central fissure) may be used for registration of the image data.

The visualization module 210 may visualize the acquired brain image data to generate a visual image. After the registration operation 930, the visualization module 210 may perform a fusion operation 951 based on the registration result. For example, the fusion operation 951 may be performed based on the images of the MRI T1 image data 921, the DTI/DTT image data 92/2, the CT/PET image data 923, the MRI TOF image data 924, and the fMRI BOLD image data 925, on which registration has been performed with the standard brain image data 926. The image fusion in the fusion operation 951 may be based on one or more fusion algorithms described above.

After the fusion operation 951, the visualization module 210 may further perform operation 952 of multi-planar reconstruction/volume rendering visualization to generate a reconstructed image. Operation 952 of multi-planar reconstruction/volume rendering visualization may utilize one or more reconstruction algorithms described above to reconstruct an image, for example, profile reconstruction, voxel reconstruction, volume rendering (VR), multi-planar reconstruction (MPR), curve planar reconstruction (CPR), maximum intensity projection (MIP), shaded surface display (SSD), or the like, or any combination thereof. The volume rendering may include volume ray casting volume rendering, unit projection, fast volume rendering algorithm, splatting volume rendering, Fourier volume rendering, shear-warp volume rendering, or the like, or any combination thereof. The reconstructed image processed by the volume rendering may show multi-modality image information, so as to facilitate disease diagnosis and/or treatment of a user (e.g., a medical worker). In some embodiments, the maximum intensity projection (MIP) may retain a pixel with a maximum intensity in an image based on an overlap image corresponding to a three-dimensional image, and project the image to two-dimensional planes such as a coronal plane, a sagittal plane, and a transverse plane, so as to form an MIP reconstructed image. For example, a two-dimensional projection image and a pixel image may be generated based on one or more three-dimensional images through the MIP. In some embodiments, operation 952 of the multi-planar reconstruction/volume rendering visualization may acquire one or more reconstructed images including a part of or all information of the MRI-T1image data 921, the DTI/DTT image data 922, the CT/PET image data 923, the MRI TOF image data 924, and/or the fMRI-BOLD image data 925. In some embodiments, the reconstructed image and/or volume rendering processed image may be displayed on the I/O 184, or stored in the database module 230, the storage device (e.g., the hard disk 182, the ROM 183, the RAM 185, the cloud storage, etc.), or the remote terminal 170.

The analysis module 220 may perform analysis on the MRI-T1image data 921, the DTI/DTT image data 922, the CT/PET image data 923, the MRI TOF image data 924, the fMRI-BOLD image data 925, the standard brain image data 926, a result of operation 930, a result of operation 951, and/or a result of operation 952, so as to generate the analysis report 945. After the registration operation 930, the analysis module 220 may simulate a result of brain tumor removal. In some embodiments, the analysis module 220 may simulate a manual removal operation of the tumor 941. According to operation 930 or operation 952, the user may manually outline a tumor range on the brain image and remove the image data in the range. The user may use the I/O 184 to implement the manual removal of the tumor. For example, the user may set one or more parameters and input one or more control signals to control the removal range of the tumor. The analysis module 220 may remove the image data in the range according to the input information of the user to implement the manual removal. As another example, the user may send control signals to the analysis module 220 through an interface to implement manual removal of the tumor in a certain range.

In some embodiments, the analysis module 220 may simulate a smart removal operation of the tumor 942. In the smart removal operation of the tumor 942, the analysis module 220 may determine a range of the tumor and surrounding information of the tumor (e.g., a name, a volume ratio, a blood flow rate, and a branching direction of a blood vessel, a count and a connection of fibers that are affected by the focus, a name and a volume ratio of a functional region that is covered by the focus, metabolic information of tissue or an organ surrounding the focus, etc.). The analysis module 220 may further analyze (operation 944) surrounding information and injury information after the tumor is removed, thereby optimizing the range of the tumor according to the injury information, automatically selecting an appropriate range of the tumor, a removal order or mode of the tumor, and removing the image data in the range. The smart removal of the tumor may indicate that the analysis module 220 performs learning one or more times to improve or optimize a determination algorithm of the range of the tumor, and automatically determines the range of the tumor, a removal order or mode of the tumor, or the like.

In some embodiments, the analysis module 220 may simulate a removal operation 943 of the entire tumor. In operation 943, the analysis module 220 may implement an extended tumor removal based on the range of the tumor determined manually and/or automatically. In some embodiments, an extended removal range of the tumor may be a range with a 2 cm, 5 cm or other distance from the tumor margin, and the extended removal range may be used for avoiding proliferation and/or recurrence of subsequent tumor cells or tumor. The analysis module 220 may further analyze (operation 944) surrounding information and injury information after the extended removal range of the entire tumor is removed, which is used as a reference of an embodiment of the removal range for, for example, a doctor. In some embodiments, the manual removal operation 941 of the tumor and the smart removal operation 942 of the tumor may belong to a non-extended removal of the tumor, and the operations are based on the surrounding information before and after the tumor removal to avoid or decrease an injury to the surrounding tissue in the image after the tumor is removed. The removal operation 943 of the entire tumor may belong to an expanded tumor removal and may avoid proliferation and/or recurrence of subsequent tumor cells or tumor.

After simulating the tumor removal, the analysis module 220 may perform an analysis operation 944 after the tumor removal. The analysis operation 944 after the tumor removal may include estimating a tumor removal result, determining injury information to the surrounding tissue after tumor removal, or the like. In some embodiments, the analysis module 220 may determine new tumor removal information according to an analysis result of previous tumor removal, so as to instruct or optimize a next manual removal operation 941 of the tumor, a next smart removal operation 942 of the tumor, or a next removal operation 943 of the entire tumor.

After the analysis operation after the tumor removal, the analysis module 220 may generate the analysis report 945. The analysis report 945 may include tumor information, tumor surrounding information, tumor removal information (e.g., a range, a time, and a mode of the tumor removal, etc.), surrounding information after the tumor removal (e.g., surrounding injury information after the tumor removal), optimized tumor removal information (e.g., a range, a time, and a mode of the optimized tumor removal, etc.), and/or any other information generated in the analysis process. In some embodiments, the analysis report 945 may further include a single-modality image, multi-modality images, a registered image, a fused image, the standard brain image 926, a reconstructed image, and/or a volume rendering processed image, or the like, or any combination thereof. In some embodiments, the analysis report 945 may further include information acquired and/or generated in the multi-modality image processing system 130 and information retrieved in the database module 230. For example, the analysis report 945 may include basic information of similar cases (e.g., a name, a gender, an age, a medical history, lab examination information, etc.), surgery information, post-surgery information (e.g., post-surgery recovery), imaging information, pathological information, or the like. In some embodiments, the analysis report 945 may be stored in the storage device (e.g., the hard disk 182, the ROM 183, the RAM 185, the cloud storage, etc.), the database module 230, or the remote terminal 170.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. A system for processing multi-modality images, comprising:
at least one storage device including a set of instructions;
at least one processor in communication with the at least one storage device, wherein when executing the set of instructions, the at least one processor is directed to cause the system to perform operations including:
obtaining multi-modality images including at least three modalities, the multi-modality images including a focus;
registering the multi-modality images;
fusing the multi-modality images by extracting effective information in the multi-modality images;
generating a reconstructed image based on a fusion result of the multi-modality images, wherein the reconstructed image includes a three-dimensional model of a target object and surrounding tissue including information of an organ or tissue, a vascular structure, nerve fibers, or a functional region of the target object; and
determining a removal range with respect to the focus based on the information of the organ or tissue, the vascular structure, the nerve fibers, or the functional region of the target object in the reconstructed image, the removal range with respect to the focus being a range that is based on the reconstructed image and larger than the focus, and includes the focus, wherein the removal range is determined based on at least a standard of avoiding or reducing injury on an area surrounding the focus on the reconstructed image.

2. The system of claim 1, wherein when executing the set of instructions, the at least one processor is directed to cause the system to perform additional operations including:
displaying image information based on the multi-modality images or the reconstructed image.

3. The system of claim 2, wherein when executing the set of instructions, the at least one processor is directed to cause the system to perform additional operations including:
obtaining a standard image, the standard image including standard image data associated with a part of the target object; and
registering the multi-modality images based on the standard image.

4. The system of claim 3, wherein the multi-modality images include multi-modality brain images.

5. The system of claim 4, wherein the displaying image information includes:

displaying information relating to blood vessels of a brain, nerve fibers, a functional region of the brain, or a metabolic rate of brain tissue.

6. The system of claim 4, wherein the multi-modality images further include a magnetic resonance imaging (MRI) T1 image, a blood oxygenation level dependent (BOLD) image, and a first image, and the first image includes one of a diffusion tensor imaging (DTI)/diffusion tensor tractography (DTT) image, a computed tomography (CT)/positron emission tomography (PET) image, or an MRI Time of Flight (TOF) image.

7. The system of claim 6, wherein the registering the multi-modality images includes:
generating a second image by registering the BOLD image based on the standard image;
generating a third image by registering the first image based on the MRI T1 image; and
registering the second image and the third image based on the MRI T1 image.

8. The system of claim 1, wherein the generating a reconstructed image includes:
segmenting the fusion result of the multi-modality images; and
generating the reconstructed image by a reconstruction algorithm based on the segmented multi-modality images, the reconstruction algorithm including multi-planar reconstruction (MPR) or volume rendering (VR).

9. The system of claim 1, wherein the determining a removal range with respect to the focus includes:
determining a range of the focus based on the reconstructed image;
determining first surrounding information of the focus based on the range of the focus, the first surrounding information including information relating to a surrounding blood vessel, information relating to a surrounding nerve, or any information relating to a tissue or organ in a vicinity of the focus; and
determining the removal range based on the first surrounding information.

10. The system of claim 9, wherein when executing the set of instructions, the at least one processor is directed to cause the system to perform additional operations including:
simulating removal of the focus based on the removal range.

11. The system of claim 9, wherein the determining the removal range further includes:
determining second surrounding information after the focus is removed;
determining, based on the first surrounding information and the second surrounding information, injury information of a surrounding tissue or organ of the focus after the focus is removed; and
optimizing the removal range based on the injury information.

12. The system of claim 11, wherein when executing the set of instructions, the at least one processor is directed to cause the system to perform additional operations including:
determining a surgery plan based on the removal range.

13. The system of claim 12, wherein when executing the set of instructions, the at least one processor is directed to cause the system to perform additional operations including:
storing case information associated with the focus, the case information including the multi-modality images, the reconstructed image, the range of the focus, the optimized removal range, the first surrounding information, the second surrounding information, the injury information, information associated with the focus, information associated with the surgery plan, or information associated with post-surgery recovery.

14. The system of claim 13, wherein when executing the set of instructions, the at least one processor is directed to cause the system to perform additional operations including:
retrieving a similar case based on the case information.

15. The system of claim 14, wherein the storing the case information associated with the focus includes storing the case information in a database; and
wherein the retrieving the similar case includes retrieving the similar case from the database.

16. The system of claim 15, wherein when executing the set of instructions, the at least one processor is directed to cause the system to perform additional operations including:
optimizing the removal range by machine learning based on information in the database.

17. The system of claim 11, wherein the focus includes a brain tumor, and the first surrounding information or the second surrounding information further includes a name of a blood vessel that the focus passes through, a blood flow rate of the blood vessel, a count of brain fibers that are affected by the focus, a connection of the brain fibers, or a name of a brain functional region that is covered by the focus.

18. The system of claim 17, wherein the injury information includes injury information of the blood vessel after the focus is removed, injury information of the brain fibers after the focus is removed, or injury information of the brain functional region after the focus is removed.

19. A method for processing multi-modality images, implemented on at least one computing device, each of the at least one computing device having at least one processor and at least one storage medium, the method comprising:
obtaining multi-modality images including at least three modalities, the multi-modality images including a focus;
registering the multi-modality images;
fusing the multi-modality images by extracting effective information in the multi-modality images;
generating a reconstructed image based on a fusion result of the multi-modality images, wherein the reconstructed image includes a three-dimensional model of a target object and surrounding tissue including information of an organ or tissue, a vascular structure, nerve fibers, or a functional region of the target object; and
determining a removal range with respect to the focus based on the information of the organ or tissue, the vascular structure, the nerve fibers, or the functional region of the target object in the reconstructed image, the removal range with respect to the focus being a range that is based on the reconstructed image and larger than the focus, and includes the focus, wherein the removal range is determined based on at least a standard of avoiding or reducing injury on an area surrounding the focus on the reconstructed image.

20. A non-transitory computer readable medium, comprising at least one set of instructions, wherein when executed by one or more processors, the at least one set of instructions directs the one or more processors to perform acts of:
obtaining multi-modality images including at least three modalities, the multi-modality images including a focus;
registering the multi-modality images;
fusing the multi-modality images by extracting effective information in the multi-modality images;
generating a reconstructed image based on a fusion result of the multi-modality images, wherein the reconstructed image includes a three-dimensional model of a target object and surrounding tissue including information of an organ or tissue, a vascular structure, nerve fibers, or a functional region of the target object; and
determining a removal range with respect to the focus based on the information of the organ or tissue, the vascular structure, the nerve fibers, or the functional region of the target object in the reconstructed image, the removal range with respect to the focus being a range that is based on the reconstructed image and larger than the focus, and includes the focus, wherein the removal range is determined based on at least a standard of avoiding or reducing injury on an area surrounding the focus on the reconstructed image.

* * * * *